(12) United States Patent
Horvath et al.

(10) Patent No.: US 8,722,892 B2
(45) Date of Patent: May 13, 2014

(54) PROCESSES AND INTERMEDIATES FOR PREPARING A MACROCYCLIC PROTEASE INHIBITOR OF HCV

(75) Inventors: Andras Horvath, Turnhout (BE); Dominique Paul Michel Depre, Hamme-Mille (BE); Dominic John Ormerod, Hoogstraten (BE)

(73) Assignee: Janssen R&D Ireland, Little Island Co Cork (IE)

( * ) Notice: Subject to any disclaimer, the term of this patent is extended or adjusted under 35 U.S.C. 154(b) by 0 days.

(21) Appl. No.: 13/484,881

(22) Filed: May 31, 2012

(65) Prior Publication Data
US 2012/0238746 A1   Sep. 20, 2012

Related U.S. Application Data

(63) Continuation of application No. 12/441,927, filed as application No. PCT/EP2008/051269 on Feb. 1, 2008, now Pat. No. 8,212,043.

(30) Foreign Application Priority Data

Feb. 1, 2007  (EP) .................... 07101571

(51) Int. Cl.
 *C07D 215/38*  (2006.01)
(52) U.S. Cl.
 USPC .......................... 546/156; 546/153
(58) Field of Classification Search
 USPC ................... 546/153, 156
 See application file for complete search history.

(56) References Cited

U.S. PATENT DOCUMENTS 8,148,399 B2 * 4/2012 Simmen et al. ............... 514/314
 8,349,869 B2 * 1/2013 Simmen et al. ............... 514/314

FOREIGN PATENT DOCUMENTS

| WO | 0059929 A1 | 10/2000 |
|---|---|---|
| WO | 2005010029 A1 | 2/2005 |
| WO | WO2005073195 A2 | 8/2005 |
| WO | WO2005073216 A2 | 8/2005 |
| WO | 2007/014926 * | 2/2007 |
| WO | 2007014926 A1 | 2/2007 |

OTHER PUBLICATIONS

Bartlett et al., Total Synthesis of Brefeldin A, Journal of the American Chemical Society, Jul. 19, 1978, p. 4858-4865, vol. 100(15).
Honda et al, A Synthesis of (+−)—Brefeldin A, Tetrahedron Letters, 1981, p. 2682-2679, vol. 22, No. 28.
Johansson, et al., Potent inhibitors of the hepatitis C virus NS3 protease: Use of a novel P2 cyclopentane-derived template, Bioorganic & Medicinal Chemistry, Aug. 1, 2006, pp. 5136-5151—XP025133411, vol. 14 No. 15.
Llinàs-Brunet, A Systematic Approach to the Optimization of Substrate-Based Inhibitors of the Hepatitis C Virus NS3 Protease: Discovery of Potent and Specific Tripeptide Inhibitors, The Journal of Medicinal Chemistry, 2004, p. 6584-6594, vol. 47, No. 26.
Rosenquist et al, Synthesis of Enantiomerically Pure trans-3,4-Substituted Cyclopentanols by Enzymatic Resolution, Acta Chemica Scandinavica, Jan. 1, 1992, p. 1127-1129, vol. 46, No. 11.

* cited by examiner

*Primary Examiner* — D M Seaman
(74) *Attorney, Agent, or Firm* — Andrea Jo Kamage

(57) ABSTRACT

The present invention relates to synthesis procedures and intermediates of a compound of formula:

(XVII)

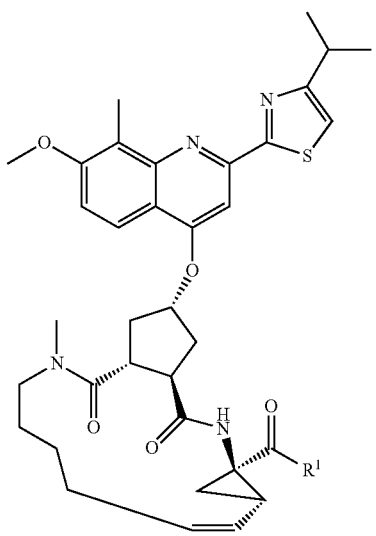

and the salts thereof.

25 Claims, No Drawings

PROCESSES AND INTERMEDIATES FOR PREPARING A MACROCYCLIC PROTEASE INHIBITOR OF HCV

CROSS REFERENCE TO RELATED APPLICATIONS

This application is a continuation of U.S. application Ser. No. 12/441,927, filed Mar. 19, 2009, currently pending, which claims priority of the benefits of the filing of European Patent Convention Application No. EP/0710571.3 filed Feb. 1, 2007, and PCT/EP2008/051269 filed Feb. 1, 2008. The complete disclosures of the aforementioned related applications are hereby incorporated herein by reference for all purposes.

FIELD OF THE INVENTION

The present invention relates to synthesis procedures and synthesis intermediates of a macrocyclic protease inhibitor of the hepatitis C virus (HCV).

BACKGROUND OF THE INVENTION

Hepatitis C virus (HCV) is the leading cause of chronic liver disease worldwide. Following initial acute infection, a majority of infected individuals develop chronic hepatitis because HCV replicates preferentially in hepatocytes but is not directly cytopathic. Chronic hepatitis can progress to liver fibrosis leading to cirrhosis, end-stage liver disease, and HCC (hepatocellular carcinoma), making it the leading cause of liver transplantations. This and the number of patients involved, has made HCV the focus of considerable medical research. Replication of the genome of HCV is mediated by a number of enzymes, amongst which is HCV NS3 serine protease and its associated cofactor, NS4A, that mediate a number of proteolytic cleavages of the HCV polyprotein resulting in the generation of the HCV replication enzymes. NS3 serine protease is considered to be essential for viral replication and has become an attractive target for drug discovery.

Current anti-HCV therapy is based on (pegylated) interferon-alpha (IFN-α) in combination with ribavirin. Not only does this therapy result in a limited efficacy in that only part of the patients are treated successfully, but it also faces significant side effects and is poorly tolerated in many patients. Hence there is a need for more effective, convenient and better-tolerated therapy. There is a need for further HCV inhibitors that overcome the disadvantages of current HCV therapy such as side effects, limited efficacy, the emergence of resistance, as well as compliance failures.

Various agents have been described that inhibit HCV NS3 serine protease and its associated cofactor, NS4A. WO 05/073195 discloses linear and macrocyclic NS3 serine protease inhibitors with a central substituted proline moiety and WO 05/073216 with a central cyclopentyl moiety. Amongst these, the macrocyclic derivatives are attractive in that they show pronounced activity against HCV and a good pharmacokinetic profile.

It now has been found that a particular macrocyclic compound with a central quinolinyloxy substituted cyclopentyl moiety is particularly attractive in terms of potency as well as pharmacokinetics. This is the compound of formula (XVII), with the structure represented hereafter:

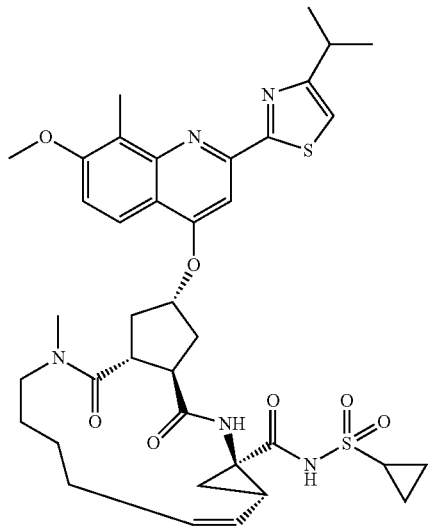

(XVII)

The compound of formula (XVII) is a very effective inhibitor of the Hepatitis C virus (HCV) serine protease and is described in WO 2007/014926, published on 8 Feb. 2007. Due to its favourable properties it has been selected as a potential candidate for development as an anti-HCV drug. Consequently there is a need for producing larger quantities of this active ingredient based on processes that provide the product in high yield and with a high degree of purity.

The present invention is concerned with processes for preparing the compound of formula (XVII), or a pharmaceutically acceptable salt thereof, with the preparation of intermediates used in these processes, and to certain of these intermediates.

The compound of formula (XVII) can be prepared by a metathesis reaction starting from an intermediate (XIV), which is cyclized to obtain an intermediate (XV), which is then hydrolyzed to the macrocyclic acid (XVI). The latter is coupled with a sulfonylamide (XVII) in an amide forming reaction, thus obtaining the end product (XVII), as outlined in the following reaction scheme:

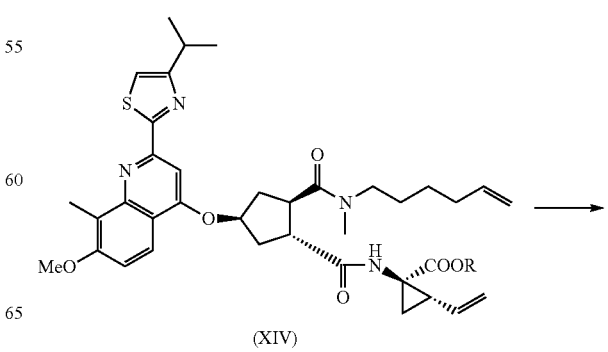

(XIV)

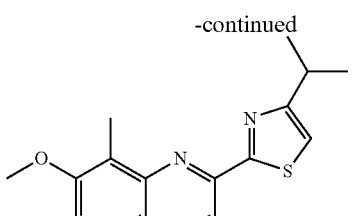

(XV)

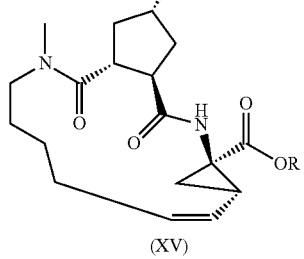

(XVI)

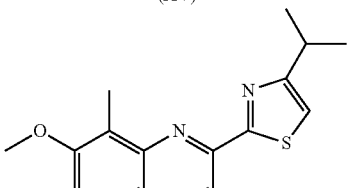

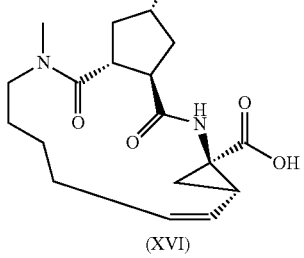

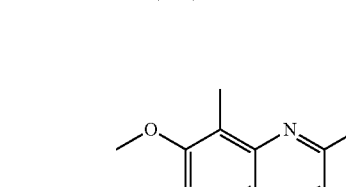

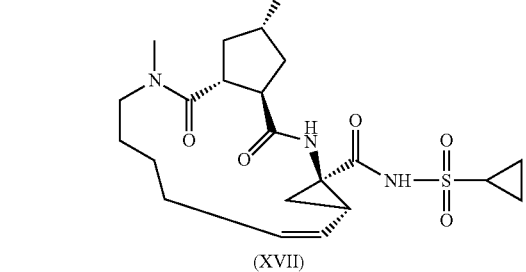

(XVII)

The pharmaceutically acceptable salt forms of the compound of formula (XVII) can be prepared by reacting the free form of this compound with an acid or with a base.

In this and the following reaction schemes or representations of individual compounds, for example in compound (XIV), R is $C_{1-4}$alkyl, in particular R is $C_{1-3}$alkyl, more in particular R is $C_{1-2}$alkyl, or in one embodiment R is ethyl. The reaction to convert (XV) into (XVI) is a hydrolysis reaction that preferably is conducted by using a base in an aqueous medium such as a mixture of water and a water-soluble organic solvent such as tertrahydrofuran (THF) or an alcohol, in particular the alcohol from which the ester in (XIV) is derived, or mixtures of such solvents. The base that is used can be an alkali metal hydroxide such as e.g. NaOH or KOH, and in particular can be LiOH.

Intermediate (XIV) is cyclized by an olefin metathesis reaction in the presence of a suitable metal catalyst such as e.g. an ylidene Ru-based catalyst, in particular an optionally substituted alkylidene or indenylidene catalyst, such as bis (tricyclohexylphosphine)-3-phenyl-1H-inden-1-ylidene ruthenium chloride (Neolyst M1®) or bis(tricyclohexylphosphine)[(phenylthio)methylene]ruthenium dichloride. Other catalysts that can be used are Grubbs first and second generation catalysts, i.e. benzylidene-bis(tricyclohexylphosphine) dichlororuthenium and (1,3-bis-(2,4,6-trimethylphenyl)-2-imidazolidinylidene)dichloro(phenylmethylene) (tricyclohexylphosphine)ruthenium, respectively. Of particular interest are the Hoveyda-Grubbs first and second generation catalysts, which are dichloro(o-isopropoxyphenylmethylene)(tricyclohexylphosphine)-ruthenium(II) and 1,3-bis-(2,4,6-trimethylphenyl)-2-imidazolidinylidene)dichloro-(o-isopropoxyphenylmethylene) ruthenium respectively. The metathesis reactions can be conducted in a suitable solvent such as for example an ether, e.g. THF, dioxane; halogenated hydrocarbons, e.g. dichoromethane, $CHCl_3$, 1,2-dichloroethane and the like, hydrocarbons, e.g. toluene. In a preferred embodiment, the metathesis reaction is conducted in toluene.

Intermediate (XVI) can be coupled with cyclopropylsulfonamide by an amide forming reaction, such as by any of the procedures for the formation of an amide bond. In particular, (XVI) may be treated with a coupling agent, for example N,N'-carbonyl-diimidazole (CDI), N-ethoxycarbonyl-2-ethoxy-1,2-dihydroquinoline (EEDQ), N-isobutyloxy-carbonyl-2-isobutyloxy-1,2-dihydroquinoline (IIDQ), 1-ethyl-3-(3'-dimethylaminopropyl)-carbodiimide (EDCI), or benzotriazol-1-yl-oxy-tris-pyrrolidinophosphonium hexafluorophosphate (commercially available as PyBOP®), in a solvent such as an ether, e.g. THF, or a halogenated hydrocarbon, e.g. dichloromethane, chlorophorm, dichloroethane, and reacted with cyclopropyl-sulfonamide, preferably after reacting (XVI) with the coupling agent. The reactions of (XVI) with cyclopropylsulfonamide preferably are conducted in the presence of a base, for example a trialkylamine such as triethylamine or diisopropylethylamine, or 1,8-diazabicycle[5.4.0]undec-7-ene (DBU). Intermediate (XVI) can also be converted into an activated form, e.g. an activated form such as an acid halide, in particular an acid chloride or bromide, or an active ester, e.g. an acid esterified with an aryloxy group such as phenoxy, p.nitrophenoxy, pentafluorophenoxy, trichlorophenoxy, pentachlorophenoxy and the like; or by converting the macrocyclic acid (XVI) into a mixed anhydride.

The intermediates (XIV) are starting materials in the preparation of the compounds of formula (XVII) and hence there is a need to provide processes for preparing these intermediates in large scale production, i.e. at multikilogram scale, or larger. These processes should provide the end product in high yield and purity. In particular the presence of various chiral centers in the molecule poses particular challenges in that chiral purity is essential to have a product that is acceptable for therapeutic use. Hence the processes for preparing (XIV) should result in products of acceptable chiral purity without use of cumbersome purification procedures with the loss of substantial amounts of undesired stereoisomeric forms.

One of the aspects of this invention concerns processes for preparing the intermediates (XIV) in high yield and purity that are fit for large scale industrial application.

The invention also concerns intermediates that are useful in the preparation of the compounds of formula (XVII). A number of such intermediates are:

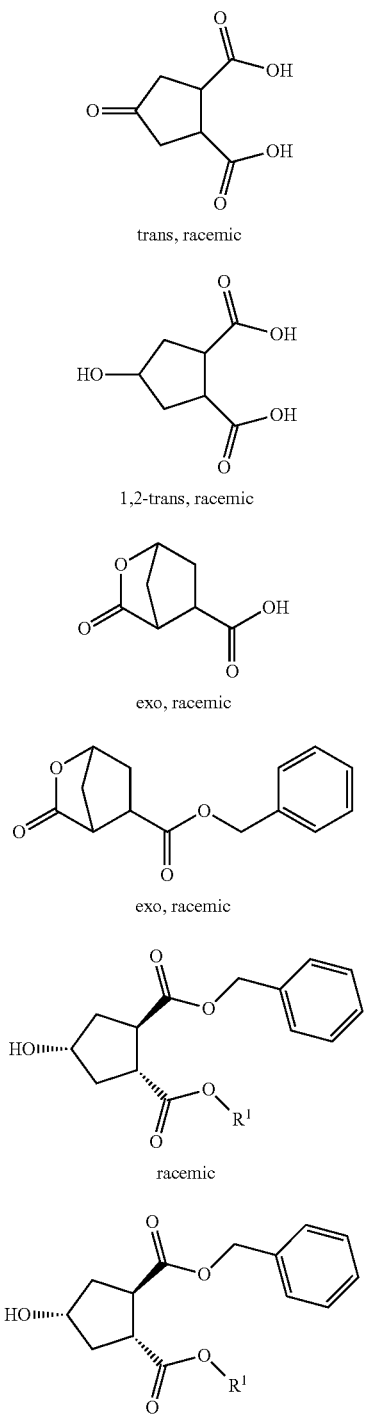

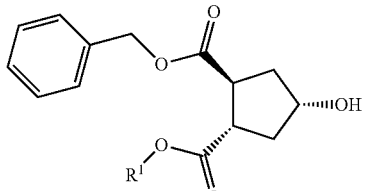

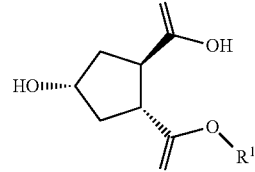

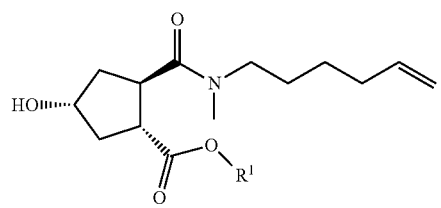

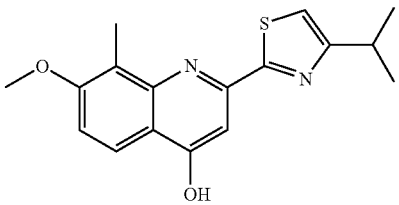

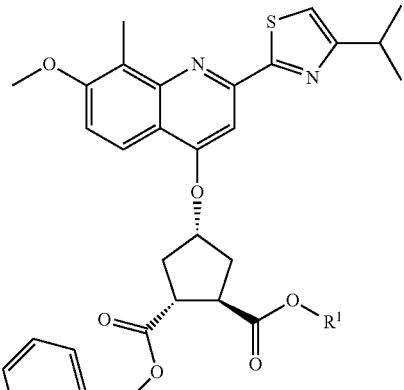

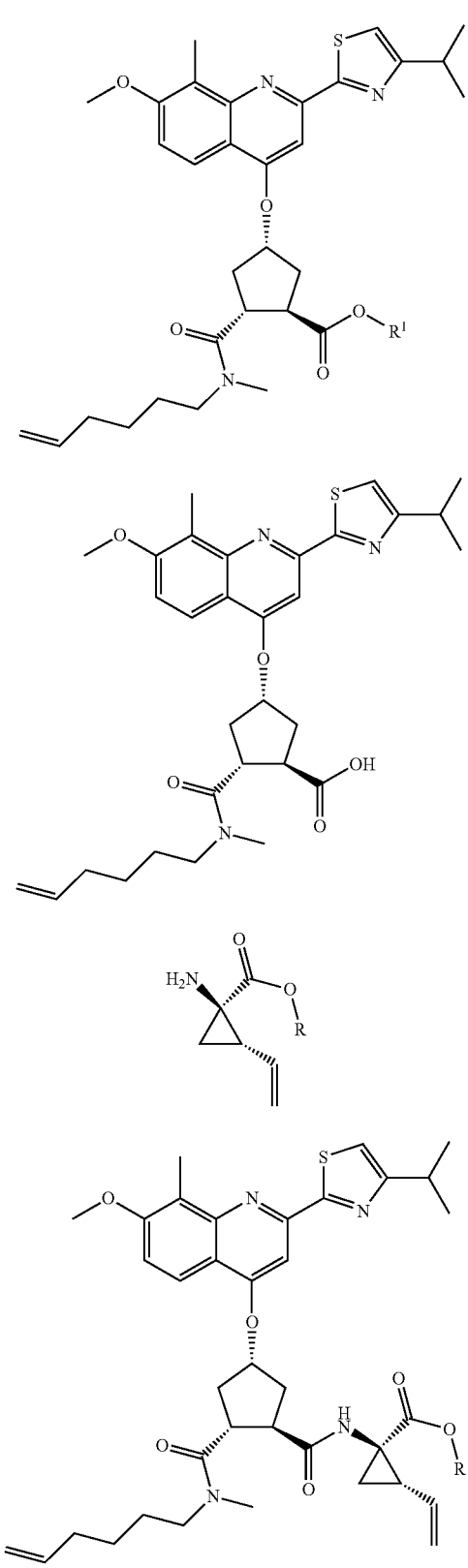

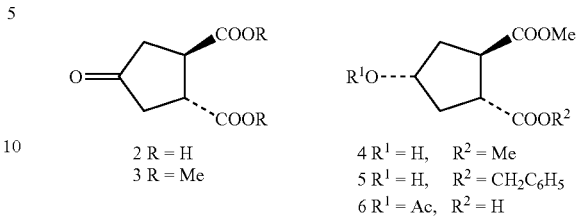

| 2 R = H | 4 $R^1$ = H, $R^2$ = Me |
| 3 R = Me | 5 $R^1$ = H, $R^2$ = $CH_2C_6H_5$ |
| | 6 $R^1$ = Ac, $R^2$ = H |

Honda et al., Tetrahedron Letters, vol. 22, no. 28, pp 2679-2682, 1981, describes the synthesis of (+)-brefeldin A using the following starting materials:

The synthesis of Honda et al. starts from dl-trans-4-oxo-cyclopentane-1,2-dicarboxylic acid (2), which was esterified to the corresponding methyl ester (3), and reduced with Raney-Ni to the alcohol (4). Partial hydrolysis of 4 and benzylation gave predominantly one diastereoisomer of the ester 5, namely that diastereoisomer wherein the hydroxyl and carboxylic acid groups are in cis position. The latter ester 5 in Honda et al. and compound (V) are both racemates, but are diastereoisomers of each other, more precisely epimers on the carbon nr. 4 bearing the hydroxy group. Compound (Va) is one of the two enantiomers obtained by separation from the racemic compound (V). The other enantiomer is compound (Vb).

WO 2005/073195 describes the synthesis of enantiomerically pure bicyclic lactone (8b) starting from an enantiomer of 3,4-bis(methoxycarbonyl)cyclopentanone. The latter was prepared as described by Rosenquist et al. in Acta Chemica Scandinavica 46 (1992) 1127-1129. The trans (3R,4R)-3,4-bis(methoxycarbonyl)cyclopentanone isomer was converted to the bicyclic lactone (8b):

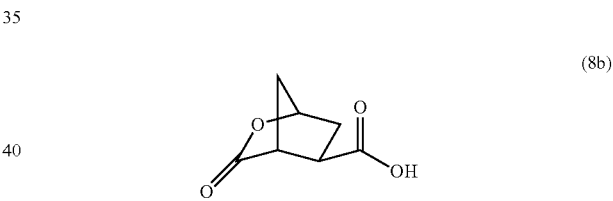

WO 2005/073195 additionally describes further modification of lactone (8b) to the t.Bu ester, opening of the lactone and coupling with appropriately protected amino acids, e.g. with (1R,2S)-1-amino-2-vinylcyclopropane carboxylic acid ethyl ester, which in the latter instance yields:

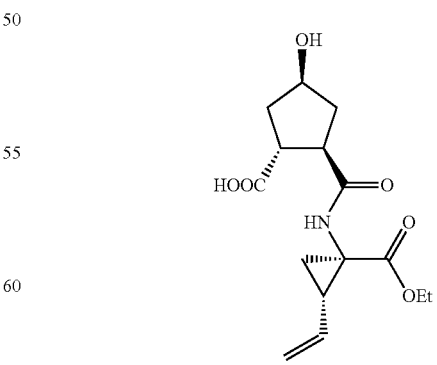

In the compounds listed in the above table, $R^1$ is a specified hereinafter and R is as specified above. In one embodiment $R^1$ is methyl. In another embodiment R is ethyl.

The build-up of the compounds of formula (XVII) necessarily involves introducing the thiazolyl substituted quinoline moiety on the cyclopentyl ring via an ether linkage. The Mitsunobu reaction offers an attractive reaction route for preparing aromatic alkylethers in which an alkyl ether is activated and reacted with an aromatic alcohol. In addition, Mitsunobu reactions are in general more efficient than the O-arylation reactions, which require additional synthesis steps. In this mild reaction the stereochemistry of the alkyl part is inverted. The reaction gives rise to side products, such as R'OOC—NH—NH—COOR', wherein R' is $C_{1-4}$alkyl and in particular ethyl or isopropyl, other nitrogen-containing compounds, and triphenylphosphine oxides, that need to be separated from the desired end product.

The processes of the present invention are advantageous in that they are suitable for large scale production. The number of cumbersome purification steps, in particular by chromatography, is reduced.

Furthermore, the choice of the protecting groups benzyl (Bn) and $C_{1-4}$alkyl, in particular methyl (Me), in the compounds (V), (Va), and (Vb) allows the selective manipulation of these compounds. The benzyl ester or the $C_{1-4}$alkyl ester (and in particular the methyl ester) can be selectively cleaved off because of the different reaction conditions used for removing a benzyl group or a $C_{1-4}$alkyl group, in particular a methyl (Me) group. Moreover, the benzyl ester moiety in compound (IV), (V), or (Va) brings the advantage that it allows efficient separation of compounds (IV), (V), or (Va) by chiral chromatography, and it facilitates the analysis and detection of these compounds since the benzyl moiety is UV-active.

DESCRIPTION OF THE INVENTION

In one aspect, the present invention relates to a process for preparing a compound of formula (XIV), starting from an intermediate (XI), which is hydrolysed to the acid (XII), which in turn is coupled with the cyclopropylamino acid ester (XIII) to obtain the desired end product (XIV), as outlined in the following reaction scheme:

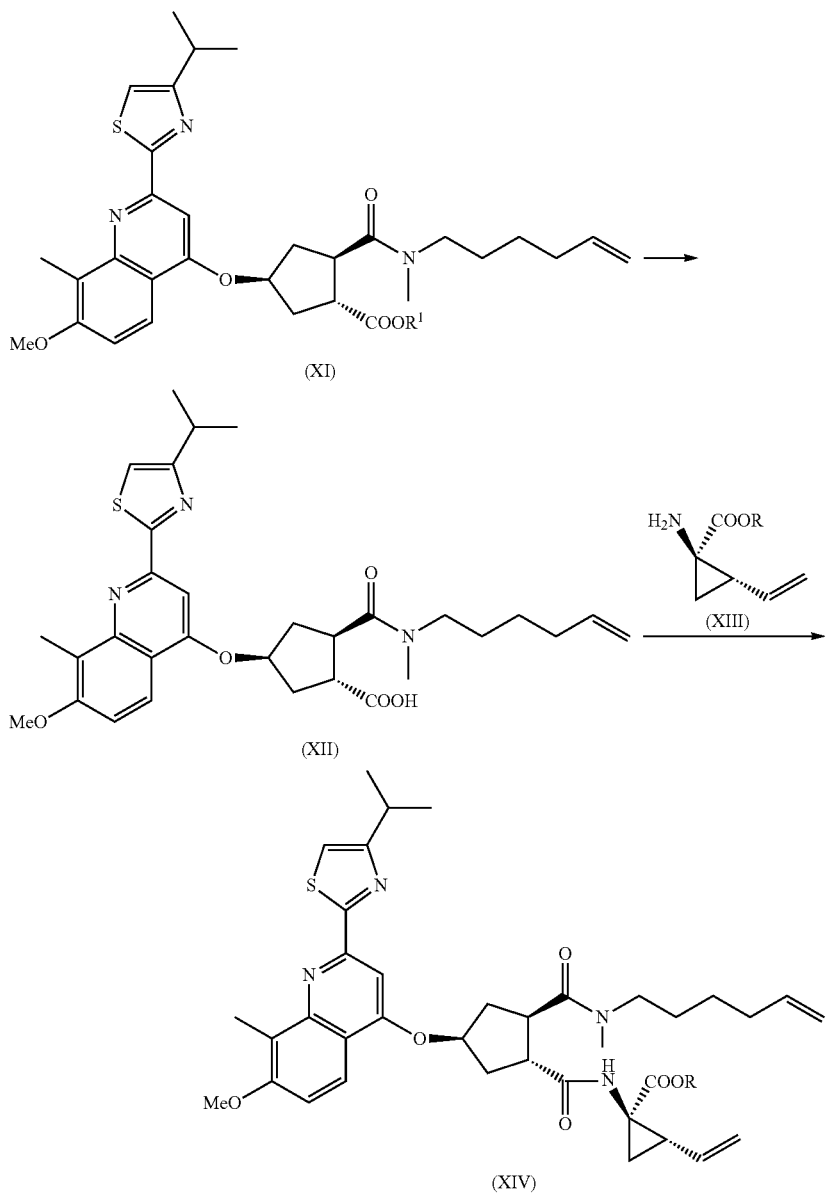

In the above scheme, R is as specified above, i.e. $C_{1-4}$alkyl, and $R^1$, independently from R, is also $C_{1-4}$alkyl. In one embodiment R is ethyl. In another embodiment $R^1$ is methyl. Of interest is a process as outlined above, and intermediates of formulae (XI), (XIII) and (XIV), wherein R is ethyl and $R^1$ is methyl.

Intermediate (XI) is the starting material in the above process and its preparation constitutes a further aspect of this invention. According to this aspect there is provided a process for preparing intermediate (XI), starting from a hydroxycyclopentyl bis-ester of formula (Va), by either (a) reacting the hydroxycyclopentyl bis-ester of formula (Va) with a thiazolyl substituted quinolinol (VIII) in an ether forming reaction, thus obtaining a quinolinyloxycyclopentyl bis-ester of formula (IX), wherein the ester group that is in cis position vis-à-vis the ether group in the quinolinyloxy-cyclopentyl bis-ester of formula (IX) is selectively cleaved to a mono carboxylic acid (X), which in turn is coupled with an alkenylamine in an amide forming reaction, thus obtaining the desired end product of formula (XI); or (b) selectively converting the hydroxycyclopentyl bis-ester of formula (Va) to the mono carboxylic acid (VI), which in turn is coupled with an alkenylamine in an amide forming reaction to obtain hydroxycyclopentylamide (VII), which in turn is reacted with a thiazolyl substituted quinolinol (VIII), thus obtaining the desired end product of formula (XI);

as outlined in the following reaction scheme:

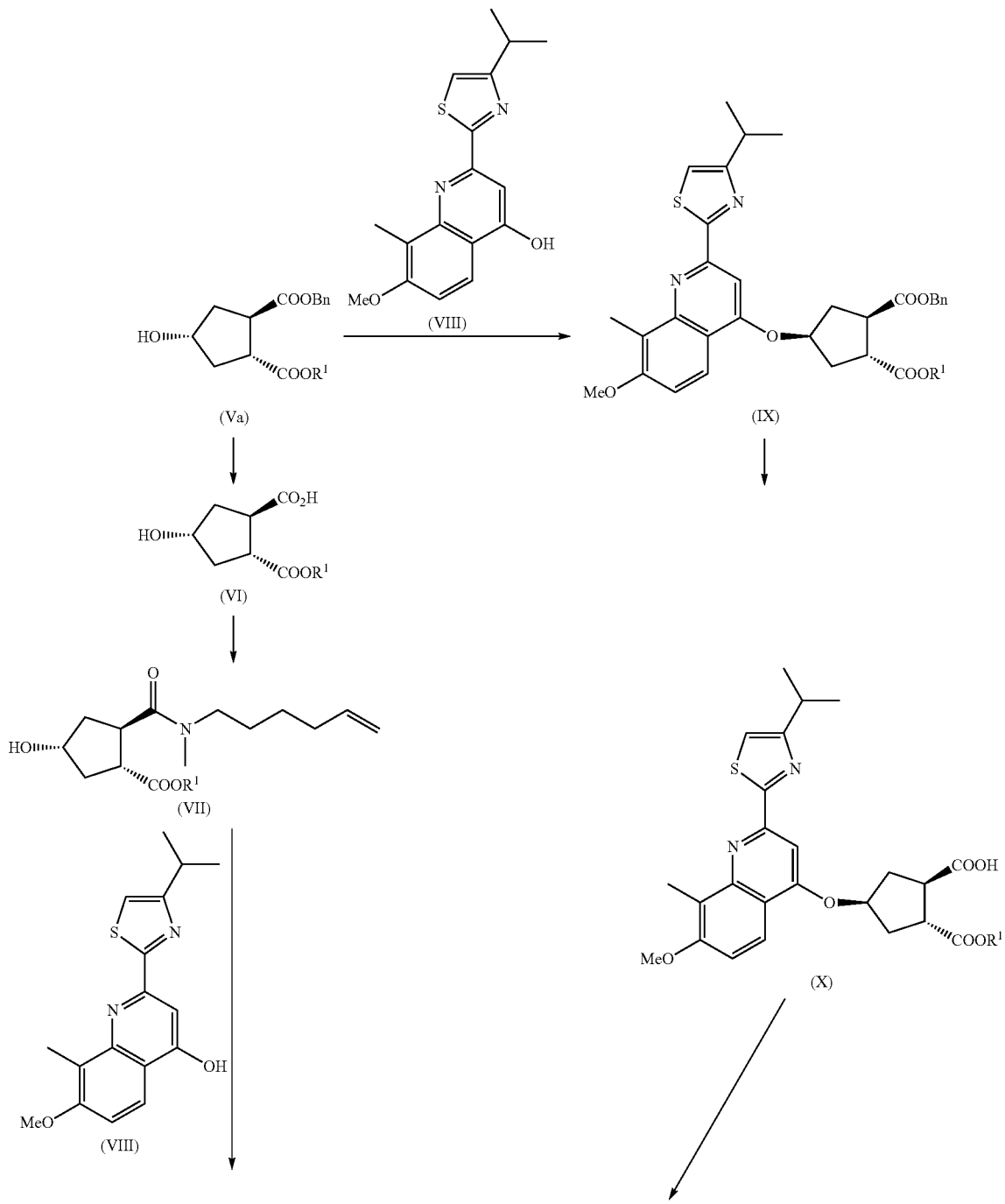

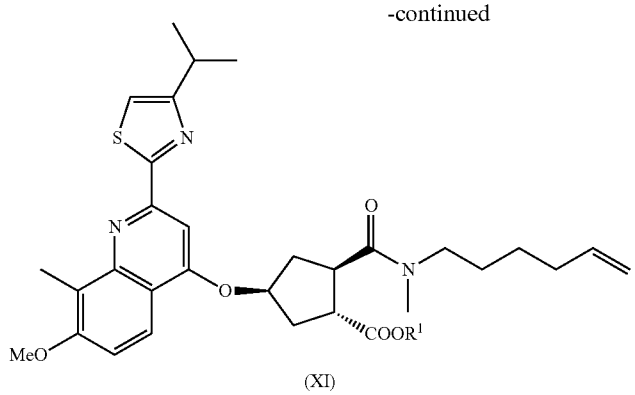

(XI)

Each R¹ in the processes represented in the above scheme and in particular in intermediates (Va), (VI), (VII), (IX), (X), and (XI) is as specified above and preferably R¹ is methyl. Bn represents benzyl.

Intermediate (Va) is the starting material in the above process and its preparation constitutes a further aspect of this invention. According to this aspect there is provided a process for preparing intermediate (Va), starting from 4-oxo-cyclopentyl-1,2-bis-carboxylic acid (I), by reducing the keto function to an alcohol, thus obtaining 4-hydroxy-cyclopentyl-1,2-bis-carboxylic acid (II), which in turn is cyclized to the bicyclic lactone (III), wherein the carboxylic acid group in the bicyclic lactone (III) is esterified with benzyl alcohol thus obtaining the lactone benzyl ester (IV), wherein the lactone is opened and the thus formed carboxylic acid group is esterified with a $C_{1-4}$alkanol thus yielding the hydroxycyclopentyl bis-ester of formula (V), which in turn is resolved in stereoisomers (Vb) and (Va); as outlined in the following reaction scheme:

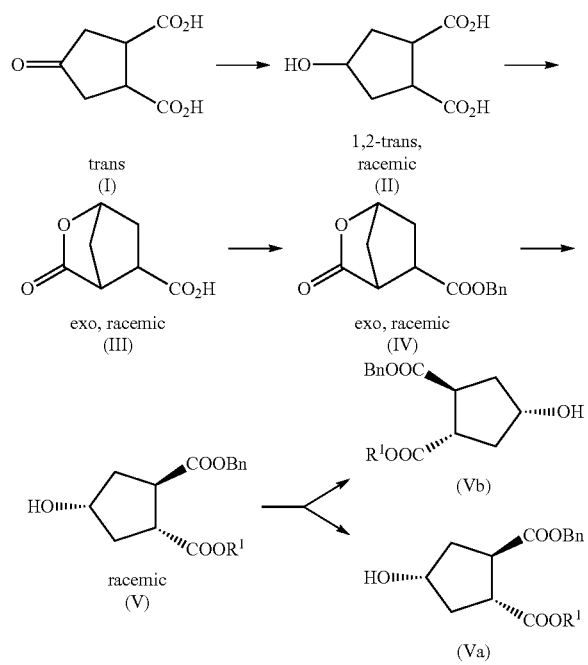

Each R¹ in the processes represented in the above scheme, and in particular in intermediates (V), (Va), and (Vb), is as specified above and preferably R¹ is methyl.

In one embodiment, the present invention relates to the use of the compounds of formula (I), (II), (III), (IV), (V), (Va), (Vb), (VI), (VII), (VIII), (IX), (X), (XI), (XII), or (XIV), as intermediates in the preparation of the compound of formula (XVII), or the salts thereof. Of particular interest are the compounds of formula (IX), (XI), (XII) and (XIV) and all intermediates leading to the formation of said compounds.

In another embodiment, the present invention relates to the compounds per se of formula (II), (III), (IV), (V), (Va), (Vb), (VI), (VII), (IX), (X), (XI), (XII), and (XIV) and the salts of the compounds of formula (II), (III), (VI), (IX), (X) and (XII). These compounds may be in isolated form, or in solution. In particular, compounds of formula (VI), (IX), (X) or (XI) are isolated in solid form.

In one embodiment, the present invention relates to a process for the preparation of the compound of formula (IX) or of formula (XI), wherein a compound of formula (Va) respectively of formula (VII) is reacted with the compound of formula (VIII) in a Mitsunobu reaction. This reacting involves reacting the starting materials with an azodicarboxylate of formula R'OOC—N=N—COOR', a phosphine of formula R"₃P, in a reaction-inert solvent; wherein
R' represents ethyl or isopropyl or t-butyl;
R" represents, each independently, phenyl, 2-pyridyl, 3-pyridyl or 4-pyridyl.

The Mitsunobu reactions presented herein are of interest in that they allow a convenient procedure for the preparation of the compounds of formula (XI) and (IX). Such preparation of the compounds of formula (XI) and (IX), when starting from compounds (VII) and (Va), respectively, comprises the inversion of the stereochemistry of the cyclopentyl carbon bearing a hydroxy or ether group.

The compounds of formula (XI) and (IX) are important intermediates because of the finding that both compounds are crystallizable, in particular when mixed with an alcoholic solvent, more in particular when mixed with a $C_{1-4}$alkanol. Crystallization of the compounds of formula (XI) and (IX) is attractive in that this allows controlling the purity of these compounds as well as any compounds derived therefrom in subsequent process steps. In particular it allows the preparation of the compounds of formula (XI) and (IX) in greater enantiomeric purity.

This crystallization of the compounds of formula (XI) and (IX) not only allows to remove the side products of the Mitsunobu reactions that yield these compounds, but also allows the subsequent separation of the compounds of formula (XI) and (IX) from their respective reaction mixtures in a simple way. This separation is easily done by effecting a solvent change, i.e. by simply adding an alcoholic solvent to the reaction mixture obtained from the Mitsunobu reactions, without having to manipulate any further the reaction mixture or any component thereof.

Further, since the compounds of formula (XI) and (IX) are not soluble in an alcoholic solvent, while the by-products are, this offers immediate purification of the compounds of formula (XI) and (IX) from the reaction mixture.

The procedures presented herein, i.e. the Mitsunobu reactions followed by a solvent change, are advantageous in large scale production. Other means of separation or purification of the compounds of formula (XI) and (IX), like chromatography, are much less suitable for large scale synthesis, require more manipulations, and involve more cost.

As used in the foregoing and hereinafter, the following definitions apply unless otherwise noted. The term halo is generic to fluoro, chloro, bromo and iodo. The term "$C_{1-4}$ alkyl" defines straight or branched chain saturated hydrocarbon radicals having from 1 to 4 carbon atoms such as for example methyl, ethyl, 1-propyl, 2-propyl, 1-butyl, 2-butyl, 2-methyl-1-propyl. Of interest are $C_{1-4}$alkyl radicals without 2-methyl-1-propyl. "$C_{1-3}$alkyl" is generic to methyl, ethyl, 1-propyl, and 2-propyl. "$C_{1-3}$alkyl" is generic to methyl and ethyl. The term $C_{1-4}$alkanol refers to an alcohol derived from a $C_{1-4}$alkyl group.

The pharmaceutically acceptable salts, which the compound of formula (XVII) can form are pharmaceutically acceptable acid-addition salts or base-addition salts. Acid-addition salts those derived from the reaction of the base form of the compound of formula (XVII) with the appropriate acid, such as, for example, an inorganic acid such as a hydrohalic acid, e.g. hydrochloric or hydrobromic acid, sulfuric, hemisulphuric, nitric, phosphoric and the like acids; or an organic acid such as, e.g., acetic, aspartic, dodecyl-sulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-amino-salicylic, pamoic and the like acids. Conversely, the acid addition salt forms can be converted into the free base form by treatment with an appropriate base. Base-addition salts are formed by treatment with appropriate organic and inorganic bases. Appropriate base-addition salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The compound of formula (XVII) has three chiral centers and getting the correct stereochemistry for all three centers is an important challenge for any synthesis processes aimed at preparing this compound. For a better understanding of the stereochemistry of the intermediates involved in the processes of the present invention, the following definitions, although known in the art, are given for reasons of clarity.

Stereoisomerism is the arrangement of atoms in molecules whose connectivity remains the same but their arrangement in space is different in each isomer. Stereoisomers can be divided into two categories of enantiomers (mirror images) and diastereoisomers (non-mirror images). The term "enantiomer" refers to one of a pair of non-superimposable mirror image molecules. Diastereomers are stereoisomers that are not enantiomers or mirror images of each other. Diastereomers can have different physical properties and different reactivity. The term "racemic" or "racemate" refers to a mixture of equal amounts of enantiomers of a chiral molecule. The term "epimer" refers to a stereoisomer that has a different configuration at only one of several stereogenic centers. Thus, the stereoisomers differ only in the configuration at a single atom.

The presently accepted convention in the nomenclature of stereochemical compounds is the following:
If a compound is drawn without stereobonds, as compound of formula (III) is drawn, then it means that it is racemic or the configuration of the stereogenic centre(s) is not defined.
If a compound is drawn with stereobonds and one of the descriptors "(±)", "rel", or "rac" is written besides the chemical structure, then it means that the compound is racemic and the stereochemistry is relative.
If a compound is drawn with stereobonds but none of the descriptors "(±)", "rel", or "rac" is written besides the structure, then it means that the compound is an optically pure compound, in other words, the stereochemistry is absolute.

For instance, in the Honda et al. reference the designation "(±)" is used in the title of the article, meaning that there is described a racemic synthesis with racemic intermediates. However the above convention may not necessarily be followed in all publications.

In one embodiment, the present invention relates to the use of a compound selected compounds (I)-(XIV), listed in the above table, as intermediates in the preparation of a compound of formula (XVII), or the salts thereof.

In another embodiment, the present invention relates to a compound of formula (II), (III), (IV), (V), (Va), (Vb), (VI), (VII), (IX), (X), (XI), (XII), or (XIV), or the salts of the compounds of formula (II), (III), (VI), (X) and (XII) as shown in the above table. The compound may be available in isolated form or in solution.

The term "isolated form", "isolated", or any equivalent thereof, refers to the solid or liquid state in which a compound is found in pure form, i.e. substantially free of other components.

In another embodiment, the present invention relates to a compound of formula (VI), (IX), (X) or (XI) wherein the compound is in solid form. The term "solid form" includes both crystalline and amorphous solid forms, or any mixture thereof.

Compound of Formula (I)

Compound of formula (I) is commercially available or may be obtained according to the procedure described in Example 1.

Step (I)→(II)

This step concerns the reduction of the keto function in the compound of formula (I) to the corresponding alcohol in the compound of formula (II). The latter is obtained by reacting the compound of formula (I) with hydrogen in the presence of a catalyst, optionally in the presence of a base. The catalyst may be selected from a noble metal catalyst such as rhodium on charcoal, rhodium on alumina, platinum on charcoal, or platinum on alumina. The base may be selected from an alkali metal hydroxide, in particular sodium hydroxide, alumina, or a tri$C_{1-4}$alkylamine such as triethylamine Upon completion of the reaction, an acid may be added to convert the salt form formed back to the free acid. This can be an inorganic acid such as a hydrohalic acid, e.g. HCl, or sulfuric acid.

Step (II)→(III)

This step involves formation of a lactone. The compound of formula (III), or a salt thereof, is obtained by reacting the compound of formula (II), or a salt thereof; with a $C_{1-4}$alkylchloroformate of formula ClCOOR$^2$, wherein R$^2$ is $C_{1-4}$alkyl, in particular methyl, ethyl, propyl, isopropyl, n-butyl, or isobutyl; and an organic base. In one embodiment, the compound of formula (III) may be isolated. The organic base may be a tertiary amine such as a tri$C_{1-4}$alkylamine, e.g. triethylamine Step (III)→(IV)

This step involves formation of a benzyl ester. The compound of formula (IV) is obtained by reacting the compound of formula (III) with benzyl alcohol; the starting material (III) and benzyl alcohol can be reacted in the presence of an ester forming agent, for example a coupling agent. Or the acid (III) can be converted into an activated form such as by reaction with a chloroformate, in particular a $C_{1-4}$alkylchloroformate of the formula ClCOOR$^2$, wherein R$^2$ is as defined above, in the presence of an organic base.

The coupling agent may be selected from the carbodiimides such as EDCI, N,N'-dicyclohexylcarbodiimide (DCC), or diisopropyl-carbodiimide, or N,N'-carbonyldiimidazole (CDI), with or without 4-dimethylaminopyridine (DMAP), or ethyl/isopropyl/isobutyl chloroformate. The organic base may be a tertiary amine such as a tri-$C_{1-4}$alkylamine, e.g. triethylamine Step (IV)→(V)

The stereoisomeric mixture (V) of the compound of formula (Va) and the compound of formula (Vb) is obtained by transesterification of the lactone to a $C_{1-4}$alkyl ester. The solvent used is preferably the alcohol from which the ester that is formed is derived, i.e. if the methyl ester is to be formed, the reaction is conducted in methanol. This is conducted in the presence of an acid catalyst and with an excess of alcohol as solvent as to drive the reaction towards ester formation. The acid catalyst may be an inorganic acid, e.g. HCl, or an organic acid such as methanesulfonic acid, or use may be made of acidic resins such as Amberlyst 15™ (A15), which can be easily removed by filtration.

Step (V)→(Va)+(Vb)

The compound of formula (Va) is obtained by separating it from compound of formula (Vb), from a mixture of the isomers (Va) and (Vb), in particular a racemic mixture of (Va) and (Vb). This enantiomeric separation may be performed by chiral phase column chromatography, or by chiral liquid chromatography. This involves using a chiral stationary phase, e.g. a polyamylose or polycellulose based stationary phase, such as Chiralpak AD™.

Step (Va)→(VI)

This step involves cleavage of the benzyl ester to the free acid. The compound of formula (VI) is prepared from the compound of formula (Va) by removal of the benzyl group by hydrogenation. This can be done by using hydrogen in the presence of a catalyst. The catalyst may be selected from palladium on charcoal, or a palladium salt or hydroxide such as palladium acetate, palladium chloride, palladium hydroxide, or palladium hydroxide on charcoal.

This reaction may be conducted in a suitable solvent, which may be selected from an ether, in particular an ether such as methyl t-butylether (MBTE), or a cyclic ether such tetrahydrofuran (THF), 2-methyl-tetrahydrofuran (MeTHF); a ketone such as acetone, methyl isobutyl ketone; an alcohol such as a $C_{1-4}$alkanol, e.g. methanol, ethanol, propanol; a dipolar aprotic solvent such as dimethylformamide (DMF), dimethylacetamide (DMA); a hydrocarbon such as toluene; or any mixture of such solvents. The reaction mixture comprising (Va), the catalyst, and the solvent may be stirred under hydrogen atmosphere. The compound of formula (VI) may be crystallized by filtering off the catalyst from the reaction mixture, washing and effecting the necessary solvent changes, for example by replacing part or all of the solvent by an ether such as MTBE, then further optionally seeding with crystal seeds of the compound of formula (VI), with optional cooling to a temperature ranging from about −15° to about 5° C. If desired, compound of formula (VI) may be obtained in a solution free from catalyst, and may be further employed in dissolved form, in the preparation of the compound of formula (VII).

Other possible debenzylation methods, which can alternatively be applied in this step, may be performed by a transfer hydrogenation using formic acid-triethylamine, Na or K formate, or by a hydrosilylation using for instance $Et_3SiH$ (TES-H), $PhSiH_3$, $Ph_2SiH_2$, poly(methylhydrosiloxane) (PMHS), or $(RO)_3SiH$.

Step (VI)→(VII)

The compound of formula (VII) is prepared from the compound of formula (VI) and N-methylhex-5-enylamine (NMHA, also referred to as N-methyl-5-hexen-1-amine) by an amide forming reaction. The latter can be any of those generally used in peptide synthesis. Use can be made of a coupling agent or the acid may be activated by converting it into a mixed anhydride or an active ester. Coupling agents that may be used can be selected from EEDQ, N,N,N,N-tetramethyl-O-(7-azabenzotriazol-1-yl)uronium hexafluorophosphate (HATU), IIDQ, benzotriazol-1-yl-oxy-tris-pyrrolidino-phosphonium hexafluorophosphate (commercially available as PyBOP®), DCC, EDCI, or 1,3-diisopropylcarbodiimide. A catalyst may be added, for example 1-hydroxybenzotriazole (HOBt). The reaction is usually conducted in the presence of a base, in particular an amine base such as a tertiary amine, e.g. triethylamine, N-methylmorpholine, N,N-diisopropylethylamine, (the latter also being referred to as or Hünig's base, DIPEA, or DIEA). The use of amide forming reactions such as O-(7-azabenzotriazol-1-yl)-N,N,N',N'-tetramethyluronium hexafluorophosphate (HATU) or O-(1H-benzotriazole-1-yl)-N,N,N',N'-tetramethyluronium hexafluorophosphate (HBTU) preferably is avoided, because of the risk of explosions at large scale production.

The coupling reaction is usually conducted in a reaction-inert solvent that may be selected from an ether, in particular a cyclic ether such as THF or MeTHF; a dipolar aprotic solvent such as DMF, hexamethylphosphoramide (HMPT), DMA, acetonitrile; a hydrocarbon such as toluene; a halogenated hydrocarbon such as dichloromethane, chloroform, 1,2-dichloroethane; an alcohol such as a $C_{1-4}$alkanol, e.g. methanol, ethanol, propanol; water; or any mixture of such solvents.

The coupling reactions are typically conducted with optional stirring at a temperature between about −20° C. and the reflux temperature of the reaction mixture.

Step (VII)+(VIII)→(XI)

This reaction step involves formation of an ether linkage between the cyclopentyl moiety in (VII) and the quinolinyl moiety in (VIII). This ether link preferably is formed via a Mitsunobu reaction. In this reaction the compound of formula (VII) is reacted with the compound of formula (VIII) in the presence of an azodicarboxylate ester of formula R'0°C.—N═N—COOR', a phosphine of formula R"$_3$P, and an organic solvent; wherein each R' represents, independently, $C_{1-4}$alkyl, in particular ethyl, isopropyl or t-butyl; and each R" represents, independently, phenyl, 2-pyridyl, 3-pyridyl or 4-pyridyl. Preferred are diethyl azodicarboxylate (DEAD) or diisopropyl azodicarboxylate (DIAD), in the presence of triphenylphosphine.

The organic solvent may be selected from a halogenated hydrocarbon such as dichloromethane, an ether, in particular a cyclic ether such as tetrahydrofuran (THF), 2-methyltetrahydrofuran (MeTHF), an ester such as ethyl acetate, isopropyl acetate, an aromatic hydrocarbon such as toluene, or any mixture of such solvents.

Optionally, a first reaction mixture comprising compound of formula (VII), compound of formula (VIII), a phosphine of formula R"$_3$P, and the organic solvent, may be partially evaporated in order to remove traces of water and/or alcohols. This first reaction mixture may be cooled at around 0° C. prior to the addition of the azodicarboxylate of formula R'OOC—N=N—COOR'. Optionally, water may be added after the addition of the azodicarboxylate, in order to remove the excess of the latter reagent. Any insoluble by-products obtained from the reaction may be removed by filtration.

Isolation of the Compound of Formula (XI)

The compound of formula (XI) is separated from the reaction mixture by changing the organic solvent, completely or partially, by a solvent selected from a C$_{1-4}$alkanol, e.g.1-buthanol, heptane, diisopropyl ether, or any mixture thereof. This change of solvent may be carried out by distilling or removing the solvents initially present in the reaction mixture, totally or partially, and by adding thereafter, one or more of the above mentioned solvents. Changing the temperature of the reaction mixture also helps in effecting crystallization. The change of solvents may be reiterated as many times and with as many solvents as desired.

The separation of the compound of formula (XI) may be carried out by filtration and drying. Crystallization of the compound of formula (XI) may also be enhanced by seeding the filtrate or reaction mixture with crystal seeds of the same compound.

Step (XI)→(XII)

In this step the ester group —COOR$^1$ in the compound of formula (XI) is cleaved off to the corresponding acid. A base in an aqueous medium can be used. Bases that can be used comprise the alkali metal hydroxides such as sodium hydroxide, or potassium hydroxide, and in particular lithium hydroxide. The aqueous medium can be water or water mixed with a water-soluble organic solvent such as an alcohol, in particular a C$_{1-4}$alkanol, e.g. methanol or ethanol; an ether, in particular a cyclic ether such as THF, MeTHF, or any mixture of such solvents The free acid of formula (XII) is obtained, or its alkali metal salt, e.g. its Li, Na, or K salt.

In one embodiment, the lithium hydroxide, sodium hydroxide, or potassium hydroxide are first mixed with the solvent prior to the addition of the compound of formula (XI). The mixture comprising compound of formula (XI); the lithium hydroxide, sodium hydroxide, or potassium hydroxide; and the solvent may be stirred at room temperature. If desired, the compound of formula (XII), or its Li, Na, or K salt, is not isolated, but used in solution for the subsequent conversion of the compound of formula (XII) into compound of formula (XIV).

Step (XII)→(XIV)

In this step the compound of formula (XII) or a salt thereof, is further reacted with the compound of formula (XIII), or a salt thereof, in an amide-forming reaction to obtain compound of formula (XIV). The same reaction conditions as described above in relation to step (VI)→(VII) can be applied.

In one embodiment, the amide-coupling agent is selected from IIDQ, EDCI, DCC, or 1,3-diisopropylcarbodiimide and in particular is EEDQ in an ether such as THF, in particular in aqueous THF. The reaction mixture above may be stirred at room temperature.

Step (Va)+(VIII)→(IX)

In this step the compound of formula (IX) is prepared, wherein compound of formula (Va) is reacted with the compound of formula (VIII) to form an ether linkage. The Mitsunobu procedure as described in step (VII)+(VIII) (XI) can be used. The compound (IX) can be crystallized by adding a C$_{1-4}$alkanol, e.g. methanol, ethanol, 1-propanol or 1-butanol. In one embodiment, water is added upon termination of the Mitsunobu reaction, and the by-products removed by filtration. The filtrate and any washings of the isolates can be concentrated to dry or almost dry and then recrystallized from a C$_{1-4}$alkanol, e.g. methanol.

Isolation of the Compound of Formula (IX)

The compound of formula (IX) can be further separated from the reaction mixture by changing the solvent, completely or partially, to a solvent selected from a C$_{1-4}$alcohol, heptane, diisopropyl ether, or any mixture thereof. This change of solvent may be carried out by distilling or removing the solvents initially present in the reaction mixture, and by adding thereafter, the solvent selected from a C$_{1-4}$alkanol, heptane, diisopropyl ether, or any mixture thereof. Changing the temperature of the reaction mixture also helps in effecting this solvent change. This change of solvents may be reiterated as many times and with as many solvents as desired.

Optionally, the separation of the compound of formula (XI) may be carried out by filtration and drying. Production of the compound of formula (XI) may also be enhanced by seeding the filtrate or reaction mixture with crystal seeds of the same compound.

Step (IX)→(X)

This step involves cleaving off the benzyl ester in (IX) to obtain the compound of formula (X). The same procedures as described above in relation to step (Va)→(VI) can be used.

Step (X)→(XI)

The compound of formula (XI) can be prepared by reacting the compound of formula (X) with NMHA and an amide-forming agent using the same procedures as described above in relation to step (VI)→(VII). Compound (XI) may be purified as described above or by recrystallization in a hydrocarbon such as hexane, heptane or octane, as described above. In one embodiment, (X) and NMHA are coupled, the reaction mixture acidified, e.g. with aqueous HCl, and extracted with a hydrocarbon, e.g. with toluene. The hydrocarbon solvent is removed and the residue recrystallized from heptane.

EXAMPLES

The following examples are intended to illustrate the present invention and not to limit it thereto.

Example 1

Preparation of the Compound of Formula (I)

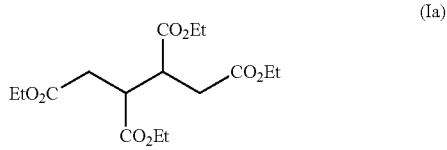 [SMILES: CCOC(=O)CC(C(=O)OCC)C(CC(=O)OCC)C(=O)OCC]

(Ia)

To a solution of 1,2,3,4-butanetetracarboxylic acid (0.99 mol, 234.16 g) in ethanol (750 ml) and toluene (500 ml) was added sulfuric acid (0.56 mol; 30.05 ml; 55.30 g) in a single portion. The mixture was heated to reflux for 4.5 h. Solvent was removed by distillation until an internal temperature of 110° C. was reached. Toluene (500 ml) was added in a single portion and the mixture heated to reflux with azeotropic removal of water using a Dean-Stark trap. After cooling to 80° C., ethanol (500 ml) was added and the mixture heated to reflux for 16 h. Solvent was removed by distillation until an internal temperature of 105° C. was reached. Toluene (500 ml) was added in a single portion and the mixture heated to reflux for 1 h with azeotropic removal of water. The mixture was cooled to 22° C., 50 ml water added and the mixture stirred for a few minutes. The two layers were separated and the toluene phase was washed with 50 ml water. The combined toluene layers were washed with aqueous sodium carbonate (15% w/w) (375.00 ml). The toluene phase was evaporated to dryness to yield a yellow oil which was also dried under vacuum at 50° C. overnight to yield 315.7 g (91% isolated yield) of the compound of formula (Ia) as a yellow colored oil.

H-NMR (CDCl₃—400 MHz), δ ppm 1.23-1.28 (m, 12 H), 2.38-2.43 (m, 2 H), 2.74-2.81 (m, 2 H), 3.28-3.31 (m, 2 H), 4.11-4.17 (m, 8 H).

IR (film) 2970, 2940, 2900, 1730, 1525, 1500, 1375, 1340.

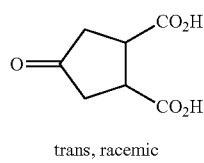

trans, racemic

To a solution of 1,2,3,4-butanetetracarboxylic acid, tetraethyl ester (1.00 mol; 346.38 g) in methanol (320.00 ml) at 22° C. was added sodium methoxide solution (30% in methanol) (2.90 mol; 522.23 g). The mixture was stirred at room temperature for 16 h. A solution of concentrated hydrogen chloride (3.49 mol; 300.00 mL; 348.90 g) and water (16.65 mol; 300.00 ml; 300 g) was added drop-wise over 15 minutes. After addition of a second portion of hydrogen chloride (1.86 mol; 160.00 ml; 186.08 g) the mixture was heated to reflux and solvent distilled off until an internal temperature of 100° C. was reached. The mixture was heated to reflux for 16 h. Then, it was cooled to 90° C. 1 g activated charcoal was added and the mixture was allowed to further cooling under stirring to 50° C. The reaction mixture was filtered over Celite. The filtrate (900 ml) was added to a 2000 ml flask. 400 ml solvent was distilled off under atmospheric pressure. Under stirring, the mixture was allowed to cool to room temperature. The solids were filtered and washed with 100 ml water. The material was dried under vacuum at 50° C. to yield 156.6 g (91% isolated yield) of the compound of formula (I) as a white solid.

H-NMR (DMSO-d6—400 MHz), δ ppm 2.32-2.38 (m, 2 H), 2.48-2.54 (m, 2 H), 3.20-3.27 (m, 2 H), 12.60 (br s, 2 H)

C-NMR (DMSO-d6—100 MHZ), δ ppm 40.70, 43.17, 174.27, 213.45.

IR (film) cm⁻¹ 3450, 3050, 2900, 1750, 1720, 1480, 1280, 1250, 1220, 1180, 1150.

Example 2

Preparation of the Compound of Formula (II)

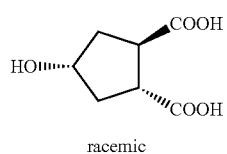

racemic

To a suspension of 32.7 g (0.19 mol) of the compound of formula (I) in 237.5 ml water under an atmosphere of nitrogen was added 1.0 ml (0.019 mol) 50% wt/wt aqueous NaOH. The mixture was warmed to 60° C. and 2.5 g Rh/C (5% wt/wt) was added. The reaction flask was purged with hydrogen and stirred under an atmosphere of hydrogen until complete conversion was reached. Then, the warm reaction mixture was filtered over Celite. The filter cake was washed twice with 10 ml water, and the filtrate was added to a 500 ml reaction flask. Then, 60 ml 4-methyl-2-pentanone was added and water was removed via azeotropic distillation until an internal temperature of 110° C. was reached. The mixture was cooled to 50° C. 88 ml acetone and 0.51 ml sulfuric acid (95%) were added. The mixture was stirred at 22° C. for 16 h. The solids were filtered and washed twice with 10 ml acetone. They were subsequently dried under vacuum at 50° C. to yield 21.84 g (66% isolated yield) of the compound of formula (II) as a white solid.

H-NMR (D₂O—400 MHz), δ ppm, 1.80-1.86 (m, 1H), 1.94-2.04 (m, 2H), 2.33-2.40 (m, 1H), 3.13 (q, J=8.5 Hz, 1H), 3.30 (q, J=8.5 Hz, 1H), 4.29-4.40 (m, 1H).

C-NMR (D₂O—100 MHZ), δ ppm, 37.61, 38.09, 44.92, 45.30, 71.67, 178.64, 178.92.

Example 3

Preparation of the Compound of Formula (III)

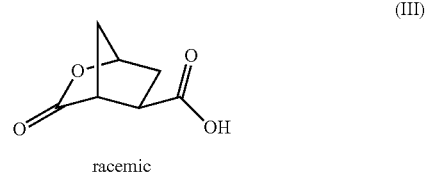 [SMILES: O=C(O)C1CC2CC1C(=O)O2]

racemic

To a suspension of the compound of formula (II) (50 g, 0.29 mol) in 860 ml THF, was added triethylamine (42.02 ml, 0.30 mol). The mixture was stirred at room temperature until complete dissolution of all solid material. Then, the reaction mixture was cooled to 0 to 5° C. Ethyl chloroformate (32.72 g, 0.30 mol) was added dropwise and the mixture stirred a further hour at 0 to 5° C. The reaction was warmed to 22° C. and stirred a further 5 h. Next, the reaction mixture was filtered over celite and the solids washed with 25 ml THF. The filtrate was evaporated to dryness. To the residue was added 50 ml ethyl acetate and the mixture was stirred at 22° C. for 15 minutes. The solids were filtered and washed with 10 ml cold ethyl acetate to yield 21.67 g (48% isolated yield) of the compound of formula (III) as a white solid.

H-NMR (CDCl₃—400 MHz), δ ppm, 1.96 (d, J=10.8 Hz, 1H), 2.27-2.29 (m, 3H), 3.05 (t, J=6.8 Hz, 1H), 3.23 (s, 1H), 5.03 (s, 1H).

C-NMR (CDCl₃—100 MHz) 32.91, 37.87, 39.90, 45.24, 80.25, 167.33, 175.54.

Example 4

Preparation of the Compound of Formula (IV)

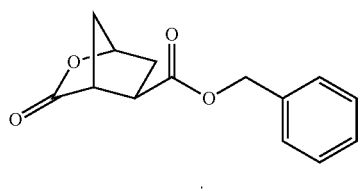

racemic 600 mg (3.84 mmol) of the compound of formula (III) (racemic), 0.418 ml (4.03 mmol) benzyl alcohol, 23.5 mg (0.19 mmol) DMAP, and 810 mg (4.23 mmol) EDCI were suspended in 38 ml ethyl acetate. The suspension was stirred over-night at room temperature. Next, 38 ml water was added, the resulting biphasic mixture was stirred at room temperature for a few minutes, then left decantating and the water layer was discarded. The organic layer was dried over magnesium sulfate, filtered and concentrated under vacuum to yield 993 mg crude compound of formula (IV) as an almost colorless oil.

993 mg crude compound of formula (IV) was purified by flash chromatography through silica gel using diisopropyl ether-hexane (3:1) as eluent. 834 mg (88% isolated yield) purified compound of formula (IV) was obtained as a colorless oil.

Physical data: GC-MS: m/z=246 (M+).

H-NMR (600 MHz, CDCl$_3$) δ ppm 1.94 (d, J=10.95 Hz, 1 H) 2.18 (d, J=10.95 Hz, 1 H) 2.22-2.27 (m, 2 H) 2.95-3.00 (m, 1 H) 3.17 (s, 1 H) 4.97 (s, 1 H) 5.18 (s, 2 H) 7.33-7.43 (m, 5 H).

C-NMR (125 MHZ, CDCl$_3$), δ ppm 33.31, 38.01, 39.77, 45.81, 67.31, 80.43, 128.27, 128.58, 128.72, 135.33, 172.37, 176.27.

350 g (1.79 mol) compound of formula (II) (racemic) and 262.1 ml (1.88 mol) triethylamine were suspended in 5.37 l THF. The mixture was cooled to 0-5° C. and 179.8 ml (1.88 mol) ethyl chloroformate was added over 1-2 h. The mixture was stirred at 0-5° C. for 2 h, then overnight at room temperature. Next, the reaction mixture was filtered and the solids were washed twice with 179 ml THF. Solvents were distilled from the filtrate and 4.48 l ethyl acetate was added to the distillation residue. To the resulting mixture, 194.6 ml (1.88 mol) benzyl alcohol, 377.6 g (1.97 mol) EDCI and 10.9 g (89.5 mol) DMAP were added. The resulting suspension was stirred overnight at room temperature. Next, 1.79 l water was added and the two layers were separated. The organic layer was dried over magnesium sulfate, filtered and concentrated to dryness under vacuum. 435 g (99% yield) crude compound of formula (IV) was obtained as a yellow oil.

Example 5

Preparation of the Compound of Formula (V)

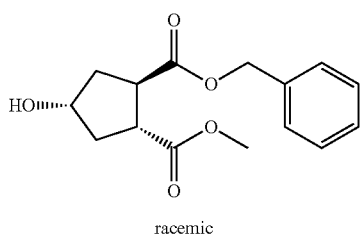

racemic 600 g (2.44 mol) compound of formula (IV) (racemic) was dissolved in 10 l methanol. 122 g Amberlyst 15 was added and the reaction mixture was stirred overnight at room temperature. The Amberlyst 15 was filtered off and the filtrate was concentrated under vacuum to yield 638 g (94% yield) crude compound of formula (V).

300 g (1.22 mol) compound of formula (IV) (racemic) was dissolved in 6 l methanol, 5 ml (0.08 mol) methanesulfonic acid was added and the reaction mixture was stirred at room temperature until disappearance of the starting material (ca 2-3 hours). Then, 90 g sodium carbonate previously dissolved in 0.9 l water was added and the mixture was concentrated under vacuum. The residue was partitioned in 1.2 l ethyl acetate and 0.6 l water. The organic layer was dried over sodium sulfate, filtered and concentrated under vacuum. 300 g (89% yield) crude compound of formula (V) was obtained as an oil.

1.75 g crude compound of formula (V) was purified by HPLC through silica gel to yield 0.55 g purified compound of formula (V).

GC-MS: m/z=278 (M+). H-NMR (400 MHz, CDCl$_3$) δ ppm 1.90-2.02 (m, 2 H) 2.07-2.17 (m, 1 H) 2.24 (ddd, 1 H) 3.14 (s, 1 H) 3.17-3.26 (m, 1 H) 3.47 (q, 1 H) 3.65 (s, 3 H) 4.32-4.39 (m, 1 H) 5.13 (br. s., 2 H) 7.26-7.39 (m, 5 H). C-NMR (100 MHz, CDCl$_3$) δ ppm 38.50, 39.63, 45.21, 45.33, 52.23, 66.60, 72.56, 127.95, 128.20, 128.53, 135.85, 174.53, 175.72.

Example 6

Preparation of the Compounds of Formula (Va) and (Vb)

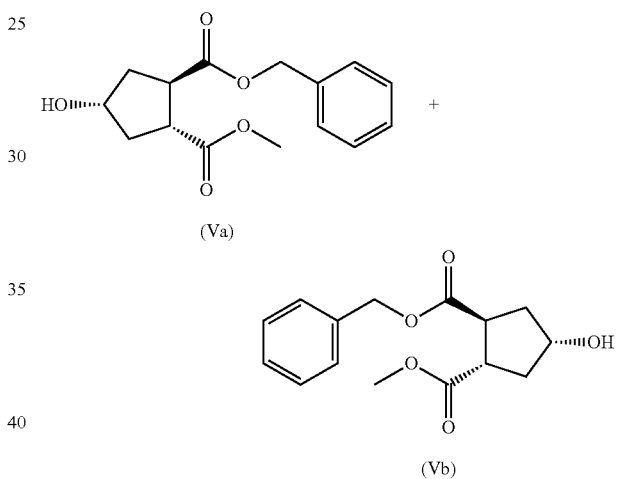

749 g crude compound of formula (V) (racemic) was eluted through Chiralpak AD using heptane/methanol/ethanol (70:15:15) as eluent to give 369 g of the compound of formula (Va) and 57 g of the compound of formula (Vb).

GC, GC-MS and NMR analyses were identical to those of the purified compound of formula (V) (racemic).

Example 7

Preparation of the Compound of Formula (VI)

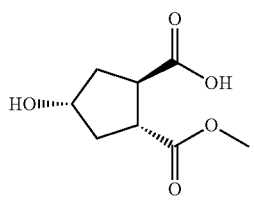

13.92 g (50 mmol) of the compound of formula (Va) and 2.66 g (2.5 mmol) dry 10% w/w Pd/C were suspended in 250 ml THF and the suspension was stirred under hydrogen atmosphere. The catalyst was filtered off and washed with a few ml THF. The filtrate was concentrated under vacuum to yield 10.80 g (114% crude yield) crude compound of formula (VI) as an oil which solidified on standing.

LC-MS: m/z=189.1 (M+H⁺).

H-NMR (400 MHz, DMSO-d₆) δ ppm 1.65-1.73 (m, 1 H) 1.74-1.81 (m, 1 H) 1.83-1.92 (m, 1 H) 2.19 (ddd, J=13.28, 10.01, 5.41 Hz, 1 H) 2.93-3.06 (m, 1 H) 3.13-3.25 (m, 1 H) 3.60 (s, 3 H) 4.08-4.22 (m, 1 H) 4.68 (s, 1 H) 12.27 (s, 1 H).

C-NMR (100 MHz, DMSO-d₆) δ ppm 38.38, 39.11, 44.31, 44.45, 51.60, 70.50, 174.43, 175.69.

123.9 g (445 mmol) of the compound of formula (Va) and 4.74 g (4.45 mmol) dry 10% w/w Pd/C were suspended in 668 ml THF. The suspension was stirred under hydrogen atmosphere. The catalyst was filtered off and washed with 228 ml THF. The filtrate was concentrated under vacuum and the residue was resuspended in 445 ml hot heptane. The suspension was allowed to cool to room temperature and 81.25 g (97% yield) compound of formula (VI) was isolated as a white crystalline material after filtration and drying.

11.13 g (40 mmol) of the compound of formula (Va) and 0.85 g (0.8 mmol) dry 10% w/w Pd/C were suspended in 60 ml THF. The suspension was stirred under hydrogen atmosphere. The catalyst was filtered off and washed 3 times with 15 ml THF. The filtrate was concentrated under vacuum and the residue was resuspended in 445 ml hot ethyl acetate. The suspension was allowed to cool to room temperature and 5.12 g (68% yield) compound of formula (VI) was isolated as a white crystalline material after filtration and drying.

20.87 g (75 mmol) of the compound of formula (Va) and 3.19 g (0.75 mmol) wet 5% w/w Pd/C were suspended in 113 ml THF. The suspension was stirred well overnight under hydrogen atmosphere. The catalyst was filtered off and washed with 19 ml THF, and 75 ml THF was distilled from the filtrate. Then, 38 ml toluene was added, and 63 ml solvent was distilled. Finally, 101 ml MTBE was added. The almost clear solution was seeded with a crystal compound of formula (VI). The suspension was cooled to −5° C. and stirred overnight at −5° C. 9.29 g (66% yield) compound of formula (VI) was isolated as a white crystalline material after filtration and drying.

6.47 g (23.3 mmol) of the compound of formula (Va) and 1.24 g (1.16 mmol) dry 10% w/w Pd/C were suspended in 23 ml DMF. The suspension was stirred well overnight under hydrogen atmosphere. The catalyst was filtered off and washed with a few ml DMF. The filtrate was brought to a volume of 50 ml with DMF, and the resulting solution was used in the next step (amide coupling with NMHA towards the formation of the compound of formula (VII)).

Example 8

Preparation of the Compound of Formula (VII)

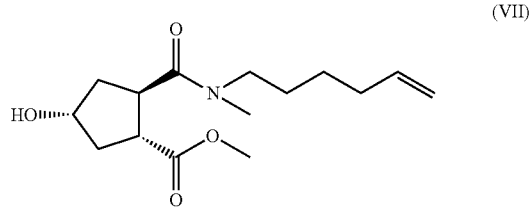 [SMILES: C=CCCCCN(C)C(=O)[C@@H]1C[C@@H](O)C[C@H]1C(=O)OC]

(VII)

303 mg (2.67 mmol) NMHA, 1.22 ml (6.99 mmol) Hunig's base and 1.06 g (2.79 mmol) HATU were added to a solution of the compound of formula (VI) in DMF (2.33 mmol in 5 ml). The mixture was stirred for 2 h at room temperature, then DMF and other volatiles were removed under vacuum. The residue was redissolved in a MeTHF-water mixture (5 ml each). 1.5 ml concentrated HCl was added, the layers were separated, and the water layer was extracted with 5 ml MeTHF. The organic layers were combined, dried over potassium carbonate and magnesium sulfate, filtered and the filtrate was concentrated under vacuum. The residue was purified by flash chromatography through silica gel using ethyl acetate as eluent. 373 mg (44% yield) of the compound of formula (VII) was obtained as a light yellow oil. NMR and GC-MS analyses showed the following compound as an impurity:

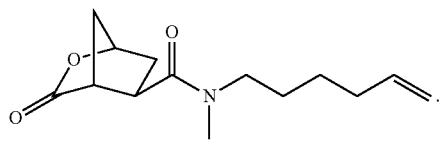 [SMILES: C=CCCCCN(C)C(=O)C1CC2CC1C(=O)O2]

GC-MS: m/z=283 (M+°)

H-NMR (600 MHz, DMSO-d₆) δ ppm 1.23-1.31 (m, 1 H) 1.33-1.40 (m, 1 H) 1.40-1.48 (m, 1 H) 1.51-1.63 (m, 2 H) 1.66-1.76 (m, 1 H) 1.80-1.91 (m, 1 H) 2.02 (q, J=7.18 Hz, 1 H) 2.07 (q, J=7.18 Hz, 1 H) 2.15-2.24 (m, 1 H) 2.80 and 2.99 (2 s—rotamers, 3 H,) 3.13-3.22 (m, 1 H) 3.25-3.33 and 3.33-3.41 (2 m—rotamers, 2 H) 3.49 (q, J=8.43 Hz, 1 H) 3.57 (s, 3 H) 4.16 (s, 1 H) 4.71 (t, 1 H) 4.91-5.09 (m, 2 H) 5.73-5.87 (m, 1 H).

C-NMR (150 MHz, DMSO-d₆) δ ppm (mixture of rotamers) 25.23 and 25.28, 26.00 and 27.61, 32.83 and 32.87, 33.20 and 34.62, 28.24 and 38.25, 39.33 and 40.13, 41.27 and 41.69, 44.92 and 45.11, 46.62, 48.67, 51.49, 70.77 and 70.81, 114.74 and 114.98, 138.38 and 138.60, 172.99 and 173.05, 174.65 and 174.68.

9.41 g (50 mmol) of the compound of formula (VI), 5.94 g (52.5 mmol) NMHA and 10.54 g (55 mmol) EDCI were suspended in 89 ml THF. The reaction mixture was stirred overnight at room temperature. 100 ml MeTHF was added and the mixture was successively washed with 50 ml water, 50 ml aqueous 0.5M HCl, 50 ml aqueous 0.5 M NaOH and 50 ml water, dried over magnesium sulfate, filtered and concentrated under vacuum. 7.54 g (53% yield) crude compound of formula (VII) was obtained as a yellow oil.

3.94 g crude compound of formula (VII) was purified by flash chromatography through silica gel using ethyl acetate as eluent to give 1.92 g purified compound of formula (VII). GC analysis showed a purity of >95%.

14.11 g (75 mmol) of the compound of formula (VI), 8.91 g (78.8 mmol) NMHA and 20.40 g (82.3 mmol) EEDQ were dissolved in 75 ml THF. The reaction mixture was stirred overnight at reflux. 1.27 g (11.3 mmol) NMHA and 2.78 g (11.3 mmol) EEDQ were added and the reflux was prolonged overnight. 63 ml solvent was distilled, and 75 ml xylene, 75 ml water and 13.5 ml concentrated HCl were added. The layers were separated and the organic layer was washed with 37.5 ml water and concentrated under vacuum, to obtain 22.47 g (106% crude yield) crude compound of formula (VII) as a light orange oil, and used in the next step as it was obtained. LC analysis showed that the main impurity was some residual xylene.

1.0 g (5.3 mmol) of the compound of formula (VI) and 1.2 g (5.8 mmol) EDCI were suspended in 10 ml dichloromethane. The suspension was stirred at room temperature until obtention of a solution (ca 15 min). Then, 0.63 g (5.6 mmol) NMHA and 6 mg (0.05 mmol) DMAP were added and the reaction mixture was stirred overnight at room temperature. Next, 10 ml ethyl acetate was added and the mixture was washed with aqueous HCl 2M, then with brine. The organic layer was concentrated under vacuum, to obtain 0.94 g (63% yield) crude compound of formula (VII) as a yellow oil. NMR analysis showed a clean product.

300 mg (1.6 mmol) of the compound of formula (VI) and 180 mg (1.6 mmol) NMHA were dissolved in 5 ml acetonitrile. Then, 0.6 g (1.6 mmol) HBTU and 0.8 ml (4.8 mmol) DIPEA were added and the mixture was stirred 2 h at room temperature. Next, 20 ml ethyl acetate was added and the mixture was washed with aqueous HCl 2M, then with brine. The organic layer was concentrated under vacuum. 1.07 g (51% yield) crude compound of formula (VII) was obtained as a brown oil.

40.0 g (0.21 mol) of the compound of formula (VI), 28 g (0.24 mol) NMHA and 63 g (0.26 mol) EEDQ were dissolved in 400 ml THF. The mixture was stirred at reflux until complete reaction then diluted with 400 ml MTBE and washed successively with 2×100 ml aqueous HCl 1M, 100 ml aqueous NaOH 1M and 50 ml brine. The organic layer was concentrated under vacuum to give 80 g crude compound of formula (VII) used in the next step as it was obtained.

Example 9

Preparation of the Compound of Formula (IX)

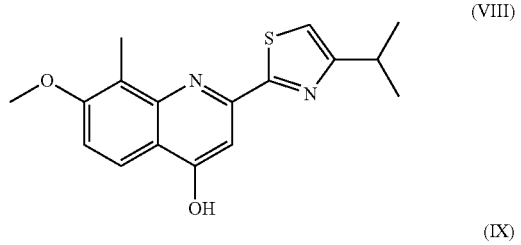

(VIII)

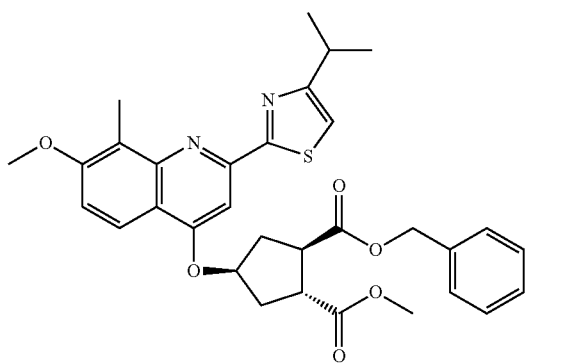

(IX)

1.7 g (5.6 mmol) of the compound of formula (Va) was dissolved in 25 ml toluene. The solution was concentrated under vacuum to dryness in order to remove any traces of water or residual alcoholic solvent. 1.57 g (5 mmol) of the compound of formula (VIII), 1.77 g (6.75 mmol) triphenylphosphine and 25 ml THF were added to the residue. The mixture was cooled to 0° C. and 1.24 ml (6.75 mmol) diisopropyl azodicarboxylate (DIAD) was added dropwise. The reaction mixture was stirred for 4 h at 0° C., then overnight at room temperature. 0.5 ml (0.5 mmol) aqueous 1M NaOH was added to destroy the excess of Mitsunobu reagent. Next, the mixture was concentrated under vacuum to dryness and the residue was eluted through silica gel with ethyl acetate as eluent. The pre-purified product was suspended in 10 ml boiling methanol, and the suspension was cooled to room temperature, stirred overnight at room temperature then 1 h at 0° C. 2.05 g (71% yield) purified compound of formula (IX) was obtained as a white powder after filtration of the suspension and drying.

Physical data: mp: 125.1° C.; $[\alpha]^D$: −9.1°; LC-MS: m/z=575 ([M+H]$^+$);

H-NMR (400 MHz, DMSO-$d_6$) δ ppm 1.33 (d, J=6.80 Hz, 6 H) 2.21-2.34 (m, 2 H) 2.41 (dd, 1 H) 2.58 (s, 3 H) 2.59-2.66 (m, 1 H) 3.14 (hept, 1 H) 3.38 (ddd, 1 H) 3.55 (dt, J=10.58, 7.93 Hz, 1 H) 3.64 (s, 3 H) 3.95 (s, 3 H) 4.98 and 5.06 (AB, J=12.34 Hz, 2 H) 5.37 (s, 1 H) 7.14-7.19 (m, 2 H) 7.22-7.28 (m, 3 H) 7.38 (d, J=9.32 Hz, 1 H) 7.45 (d, J=3.78 Hz, 2 H) 7.88 (d, J=9.32 Hz, 1 H);

C-NMR (100 MHz, DMSO-$d_6$) δ ppm 9.77, 22.30, 30.40, 35.10, 35.93, 44.66, 45.02, 51.90, 56.08, 66.00, 78.70, 95.35, 112.83, 115.50, 116.07, 120.07, 120.25, 127.60, 127.91, 128.25, 135.80, 147.86, 151.17, 157.96, 160.31, 164.27, 168.64, 173.12, 173.86.

20.75 g (74.5 mmol) Compound of formula (Va), 26.25 g (71 mmol) Compound of formula (VIII) and 28 g (110 mmol) triphenylphosphine are dissolved in 391 ml toluene. 50 ml of toluene is distilled off in order to remove any traces of water or residual alcoholic solvent. The mixture is cooled to 0° C. and 21.58 g (110 mmol) DIAD is added dropwise. The reaction mixture is stirred for 2 h at 0° C. 7.1 ml water is added to destroy the excess of Mitsunobu reagent. The mixture is stirred at room temperature for 10 minutes then by-products of Mitsunobu are filtered off and washed with 25 ml toluene. The filtrate and washing layers are concentrated under vacuum and the hot oily residue is diluted with 355 ml methanol. The mixture is cooled to 0° C. then stirred overnight at 0° C. 30.6 g (75% yield) Compound of formula (IX) is obtained as a white powder after filtration of the suspension and drying.

Example 10

Preparation of the Compound of Formula (X)

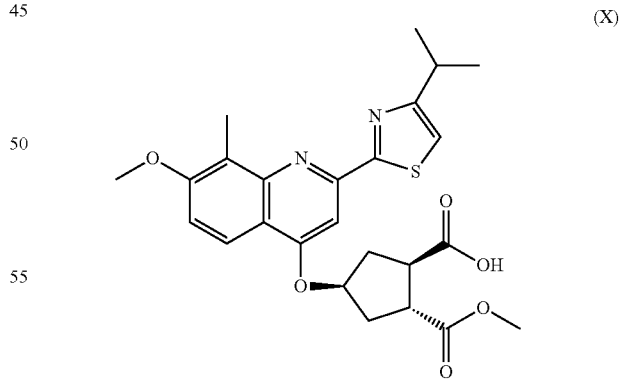

(X)

1.50 g (2.61 mmol) of the compound of formula (IX) and 1.25 ml (7.83 mmol) triethylsilane were dissolved in 2.6 ml THF. 29.3 mg (0.13 mmol) palladium acetate was added and the mixture was stirred overnight at reflux. The mixture was cooled to room temperature. Then, 150 mg Norit A Supra, 150 mg dicalite and 0.2 ml aqueous 1N HCl were added and the mixture was refluxed for 2-3 hours. The mixture was filtered hot and the filtrate was concentrated under vacuum to dryness. The residue was suspended in 2 ml boiling methanol. The suspension was cooled to 0° C. and further stirred for 1-2 h. 800 mg (63% yield) compound of formula (X) was obtained as a white powder after filtration and drying.

Physical data: mp: 161.3° C.; LC-MS: m/z=483 ([M−H]⁻);
H-NMR (400 MHz, DMSO-$d_6$) δ ppm 1.34 (d, J=7.05 Hz, 6 H) 2.19-2.30 (m, 2 H) 2.38 (dd, J=13.85, 7.81 Hz, 1 H) 2.58 (s, 3 H) 2.60 (ddd, J=9.88, 4.85, 4.66 Hz, 1 H) 3.15 (hept, 1 H) 3.23 (ddd, 1 H) 3.49 (ddd, J=10.70, 7.93, 7.81 Hz, 1 H) 3.67 (s, 3 H) 3.96 (s, 3 H) 5.34 (s, 1 H) 7.40 (d, J=9.32 Hz, 1 H) 7.44 (d, J=0.76 Hz, 1 H) 7.46 (s, 1 H) 7.96 (d, J=9.06 Hz, 1 H) 12.47 (s, 1 H);
C-NMR (100 MHz, DMSO-$d_6$) δ ppm 9.77, 22.30, 30.40, 35.35, 36.06, 44.57, 45.09, 51.84, 56.05, 78.72, 95.30, 112.77, 115.44, 116.12, 120.07, 120.36, 147.83, 151.18, 157.94, 160.42, 164.25, 168.65, 174.11, 174.74.

4.48 g (7.79 mmol) of the compound of formula (IX), 3.74 ml (23.37 mmol) triethylsilane and 87 mg (0.39 mmol) palladium acetate were dissolved in 8 ml MeTHF. The mixture was stirred overnight at reflux. The mixture was cooled to 60° C. 220 mg Norit A Supra, 220 mg dicalite, 0.52 ml water and 0.6 ml concentrated HCl were added and the mixture was refluxed for 1-2 hours. The mixture was cooled to 50-55° C., filtered and the solid was washed with 8 ml MeTHF. The filtrate and the washing were combined and the resulting solution (15.4 g solution—25% w/w compound of formula (X)) was used in the next step.

Example 11

Preparation of the Compound of Formula (XI)

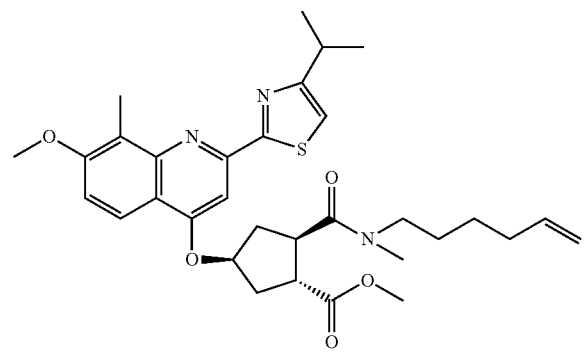

(XI)

11.49 g (34.58 mmol) of the compound of formula (VIII) and 9.52 g (36.30 mmol) triphenylphosphine were added to a solution of the compound of formula (VII) in toluene (34.58 mmol compound of formula (VII) for 184.86 g solution). 64 ml of solvent was distilled off in order to remove traces of water and/or alcohols, then the mixture was cooled to 0° C. 7.2 ml (36.30 mmol) DIAD was added. The mixture was stirred 2 hours at 0° C. After analysis, additional triphenylphosphine (0.9 g, 3.46 mmol) and DIAD (0.68 ml, 3.46 mmol) were added at 0° C. and the mixture stirred further at 0° C. for 1 hour, then allowed to warm to room temperature over 15 hours with stirring. The mixture was then cooled and stirred further for 1-2 hours at 0° C., after which the precipitated solid material was filtered off and rinsed with 17 ml of toluene (the solid consists of mostly triphenylphosphine oxide, 18 g wet weight). 140 ml solvent was distilled from the filtrate and 103.7 ml n-butanol was added. Distillation was continued and 88 ml solvents were distilled off, then the mixture was cooled to 80° C. and 103.7 ml isopropanol and 1.73 g dicalite were added. The mixture was filtered hot. The filtrate was cooled to 30° C., seeded with the compound of formula (XI), cooled and stirred at 0° C. for 56 hours. The mixture was filtered, the filtercake washed with 10.4 ml cold isopropanol and the product dried at 70° C. in vacuum. Yield: 15.00 g (71%).

Physical data: mp: 130.7° C.; [α]D: −12.6°; LC-MS: m/z=580 ([M+H]+).

H-NMR (400 MHz, DMSO-$d_6$, mixture of rotamers) δ ppm 1.19 (m, 2 H—one rotamer) 1.34 (d, J=6.80 Hz, 6 H) 1.36-1.43 (m, 4 H—one rotamer) 1.46-1.61 (m, 2 H—one rotamer) 1.76-1.87 (m, 1 H) 1.92 (q, J=6.80 Hz, 2 H—one rotamer) and 2.07 (q, J=6.88 Hz, 2 H—one rotamer) 2.20-2.40 (m, 2 H) 2.58 (s, 3 H) 2.71-2.78 (m, 1 H) 2.79 (s, 3 H—one rotamer) and 2.98 (s, 3 H—one rotamer) 3.14 (hept, J=6.75 Hz, 1 H) 3.21-3.52 (m, 4 H) 3.62 (s, 3 H) 3.62-3.70 (m, 1 H) 3.96 (s, 3 H) 4.86 (dd, J=10.20, 0.88 Hz, 1 H—one rotamer) 4.92 (dd, J=18.13, 1.51 Hz, 1 H—one rotamer) 4.96 (dd, J=11.08, 1.00 Hz, 1 H—one rotamer) 5.03 (dd, J=17.12, 1.51 Hz, 1 H—one rotamer) 5.33 (s, 1 H) 5.68 (ddt, J=17.12, 10.32, 6.74 Hz, 1 H—one rotamer) and 5.81 (ddt, J=17.00, 10.20, 6.68 Hz, 1 H—one rotamer) 7.40-7.48 (m, 3 H) 8.03 (d, J=8.81 Hz, 1 H—one rotamer) and 8.04 (d, J=9.06 Hz, 1 H—one rotamer) C-NMR (100 MHz, DMSO-$d_6$, mixture of rotamers) δ ppm 9.77, 22.26, 22.80, 25.14, 25.23, 25.90, 27.56, 30.40, 32.75, 32.86, 33.12, 34.61, 35.68, 35.73, 36.21, 36.76, 42.20, 42.61, 44.92, 45.19, 46.67, 48.58, 51.62, 51.65, 56.06, 78.23, 78.30, 95.35, 95.39, 112.77, 112.86, 114.61, 114.89, 115.47, 116.13, 116.17, 119.99, 120.03, 120.50, 120.56, 138.41, 138.49, 147.83, 147.85, 151.19, 151.20, 157.98, 158.00, 160.55, 160.58, 164.22, 168.64, 168.67, 171.93, 173.95, 174.10.

730 mg (1.51 mmol) of the compound of formula (X) and 213 mg (1.88 mmol) NMHA were dissolved in a mixture THF-MeTHF (3 ml+3 ml). The mixture was heated to 50° C. Then, 465 mg (1.88 mmol) EEDQ was added and the mixture was stirred overnight at 50° C. 43 mg (0.38 mmol) NMHA and 93 mg (0.38 mmol) EEDQ were added and the mixture was stirred 2 days at 50° C. The mixture was concentrated under vacuum then redissolved in 3 ml MeTHF and successively washed with 6 ml aqueous 1N HCl, 3 ml water and 1.5 ml brine. The organic layer was dried over magnesium sulfate. The solid was filtered off and the filtrate was concentrated to dryness under vacuum. 0.95 g crude compound of formula (XI) was obtained as an off-white solid.

The crude solid was resuspended in 6 ml boiling heptane. The suspension was cooled to room temperature and further stirred overnight at room temperature. 710 mg (81% yield) purified compound of formula (XI) was obtained as a white powder after filtration and drying.

1.23 g (10.9 mmol) NMHA and 2.69 g (10.9 mmol) EEDQ were added to 15.4 g of 25% w/w compound of formula (X) solution in MeTHF (7.8 mmol compound of formula (X)). The mixture was stirred overnight at 50° C. then cooled to room temperature. Then, 28 ml water, 3.1 ml concentrated HCl and 10 ml toluene were added, the resulting layers were separated and the organic layer was washed with 16 ml water. The organic layer was treated with 2.38 g basic alumina, 1.94 g dicalite and 1.01 g Norit A Supra and filtered. The filtrate was concentrated under vacuum and the residue was suspended in 51 ml heptane. The suspension was stirred overnight at room temperature then 2 h at 0° C. 2.25 g (50% yield) of the compound of formula (XI) was obtained after filtration and drying.

Example 12

Preparation of the Compound of Formula (XII)

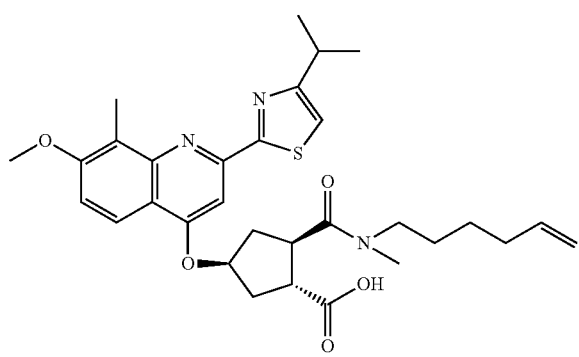

(XII)

600 mg (1.03 mmol) of the compound of formula (XI) was dissolved in 4.1 ml THF, then 45.6 mg (1.1 mmol) LiOH.H$_2$O previously dissolved in 1 ml water was added. The resulting mixture was stirred 2-3 hours at room temperature. LC and LC-MS analyses showed the almost complete conversion of the compound of formula (XI) into compound of formula (XII). This solution was used in the next step as it was obtained.

Physical data: LC-MS: m/z=564 ([M−H]$^-$).

Example 13

Preparation of the Compound of Formula (XIV)

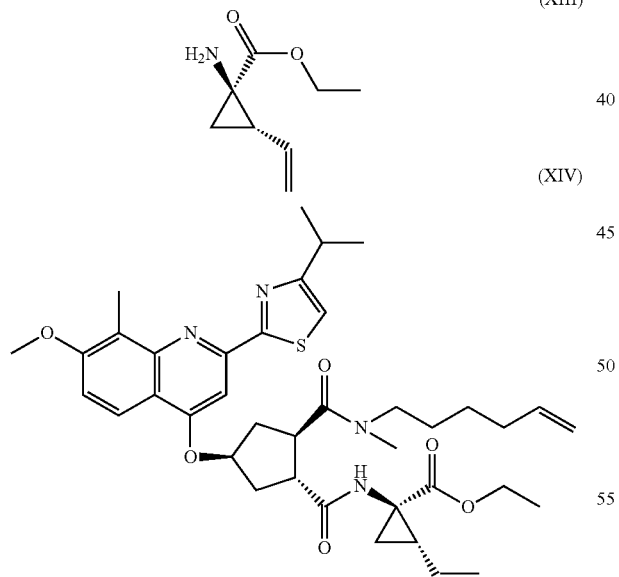

1.14 mmol of the compound of formula (XIII) and 294 mg (1.19 mmol) EEDQ were added to 1.03 mmol of the compound of formula (XII) Li-salt in solution in THF-water (4.1 ml+1 ml). The mixture was stirred overnight at room temperature. Then, 2.1 ml toluene and 1.55 ml aqueous 1N HCl were added. The two layers were separated and the organic layer was successively washed with 0.52 ml water, 1.55 ml aqueous 1N NaOH, 0.52 ml water, and 0.52 ml brine. The organic layer was then dried over sodium sulfate. The solids were filtered off and the filtrate was concentrated to dryness under vacuum. 698 mg (96% yield) crude compound of formula (XIV) was obtained as glassy compound. NMR and LC analyses showed a >90% purity.

Physical data: LC-MS: m/z=703 ([M+H]$^+$).

H-NMR (400 MHz, DMSO-d$_6$—mixture of rotamers) δ ppm 0.87 (t, J=7.30 Hz, 1H) 1.06-1.19 (m, 3 H) 1.19-1.31 (m, 2 H) 1.33 (d, J=6.80 Hz, 6 H) 1.35-1.45 (m, 2 H) 1.46-1.66 (m, 2 H) 1.84-2.00 (m, 2 H) 2.00-2.18 (m, 3 H) 2.25-2.36 (m, 1 H) 2.58 (s, 3 H) 2.64-2.77 (m, 1 H) 2.80 (s, 3 H—one rotamer) 3.00 (s, 3 H—one rotamer) 3.08-3.30 (m, 2 H) 3.34-3.52 (m, 3 H) 3.97 (s, 3 H) 3.98-4.12 (m, 2 H) 4.82-5.13 (m, 3 H) 5.18-5.37 (m, 2 H) 5.55-5.86 (m, 2 H) 7.39-7.50 (m, 3 H) 8.06 (t, J=8.94 Hz, 1 H) 8.59 (s, 1 H—one rotamer) 8.73 (s, 1 H—one rotamer).

C-NMR (100 MHz, DMSO-d$_6$—mixture of rotamers) δ ppm 9.79, 13.80, 13.96, 13.99, 14.12, 14.53, 18.59, 22.21, 22.30, 25.25, 25.32, 26.02, 27.64, 30.40, 32.07, 32.14, 32.81, 33.19, 34.64, 34.68, 36.31, 36.76, 36.95, 36.98, 42.28, 46.01, 46.43, 46.74, 48.74, 56.10, 60.33, 60.51, 60.59, 78.73, 78.80, 95.34, 95.38, 112.67, 112.76, 114.67, 114.88, 115.47, 116.20, 116.23, 117.34, 120.03, 120.05, 120.59, 120.62, 134.13, 134.18, 138.41, 138.49, 147.85, 151.22, 157.98, 158.0, 160.75, 164.25, 168.66, 168.69, 169.82, 169.85, 172.48, 172.51, 173.66, 173.83.

The invention claimed is:

1. A process for preparing a compound of formula (XVII) starting from an intermediate (XIV), followed by cyclization to obtain an intermediate (XV), followed by hydrolysis to the macrocyclic acid (XVI); followed by coupling with cyclopropylsulfonylamide in an amide forming reaction, thus obtaining the end product (XVII), as outlined in the following reaction scheme:

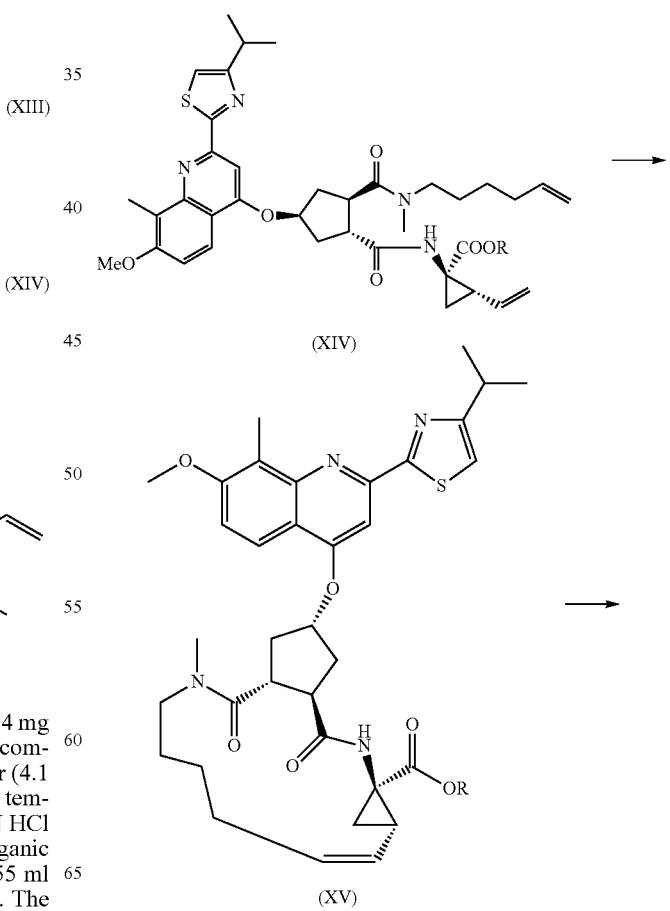

-continued

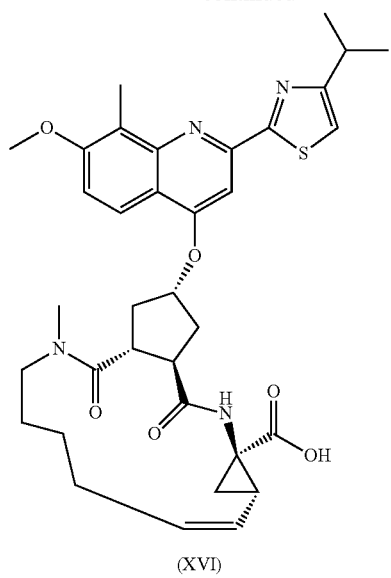

(XVI)

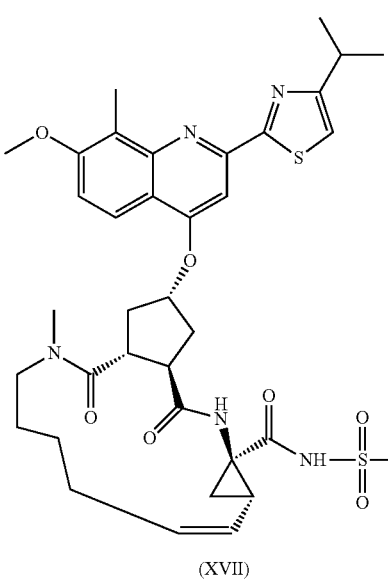

(XVII)

and wherein the compound of formula (XIV) is prepared by a process starting from an intermediate (XI), which is hydrolysed to the acid (XII), which in turn is coupled with the cyclopropylamino acid ester (XIII) to obtain the desired end product (XIV), as outlined in the following reaction scheme:

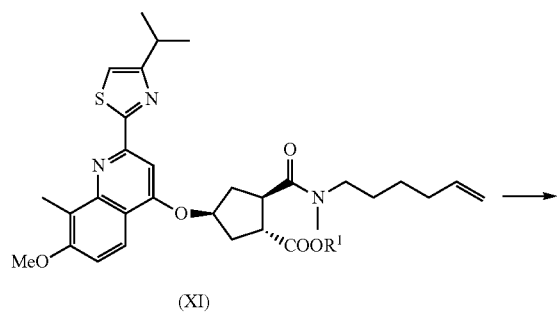

(XI)

-continued

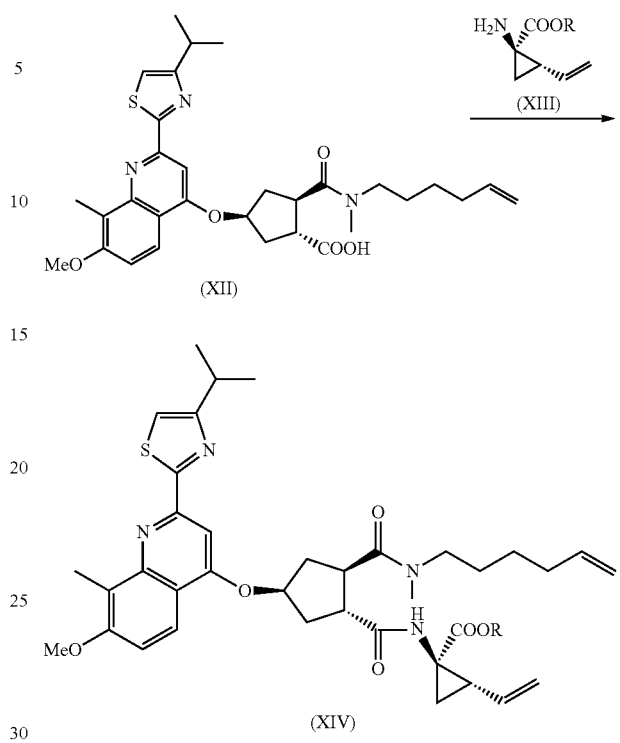

wherein R is $C_{1-4}$alkyl, and $R^1$, independently from R, is also $C_{1-4}$alkyl.

2. The process according to claim 1, wherein the compound of formula (XI) is reacted with an alkali metal hydroxide, to obtain compound of formula (XII), or its alkali metal salt.

3. The process according to claim 1, wherein the compound of formula (XII) or a salt thereof, is further reacted with the compound of formula (XIII), or a salt thereof, and an amide-coupling agent, to obtain compound of formula (XIV).

4. A process according to claim 1, wherein the compound of formula (XIV) is prepared by a process for preparing a compound of formula (XI), or a salt thereof, starting from a hydroxycyclopentyl bis-ester of formula (Va), by either (a) reacting the hydroxycyclopentyl bis-ester of formula (Va) with a thiazolyl substituted quinolinol (VIII) in an ether forming reaction, thus obtaining a quinolinyloxycyclopentyl bis-ester of formula (IX), wherein the ester group that is in cis position vis-áé-vis the ether group in the quinolinyloxy-cyclopentyl bis-ester of formula (IX) is selectively cleaved to a mono carboxylic acid (X), which in turn is coupled with an alkenylamine in an amide forming reaction, thus obtaining the desired product of formula (XI); or (b) selectively converting the hydroxycyclopentyl bis-ester of formula (Va) to the mono carboxylic acid (VI), which in turn is coupled with an alkenylamine in an amide forming reaction to obtain hydroxycyclopentylamide (VII), which in turn is reacted with a thiazolyl substituted quinolinol (VIII), thus obtaining the desired product of formula (XI);

as outlined in the following reaction scheme, wherein $R^1$ represents $C_{1-4}$alkyl:

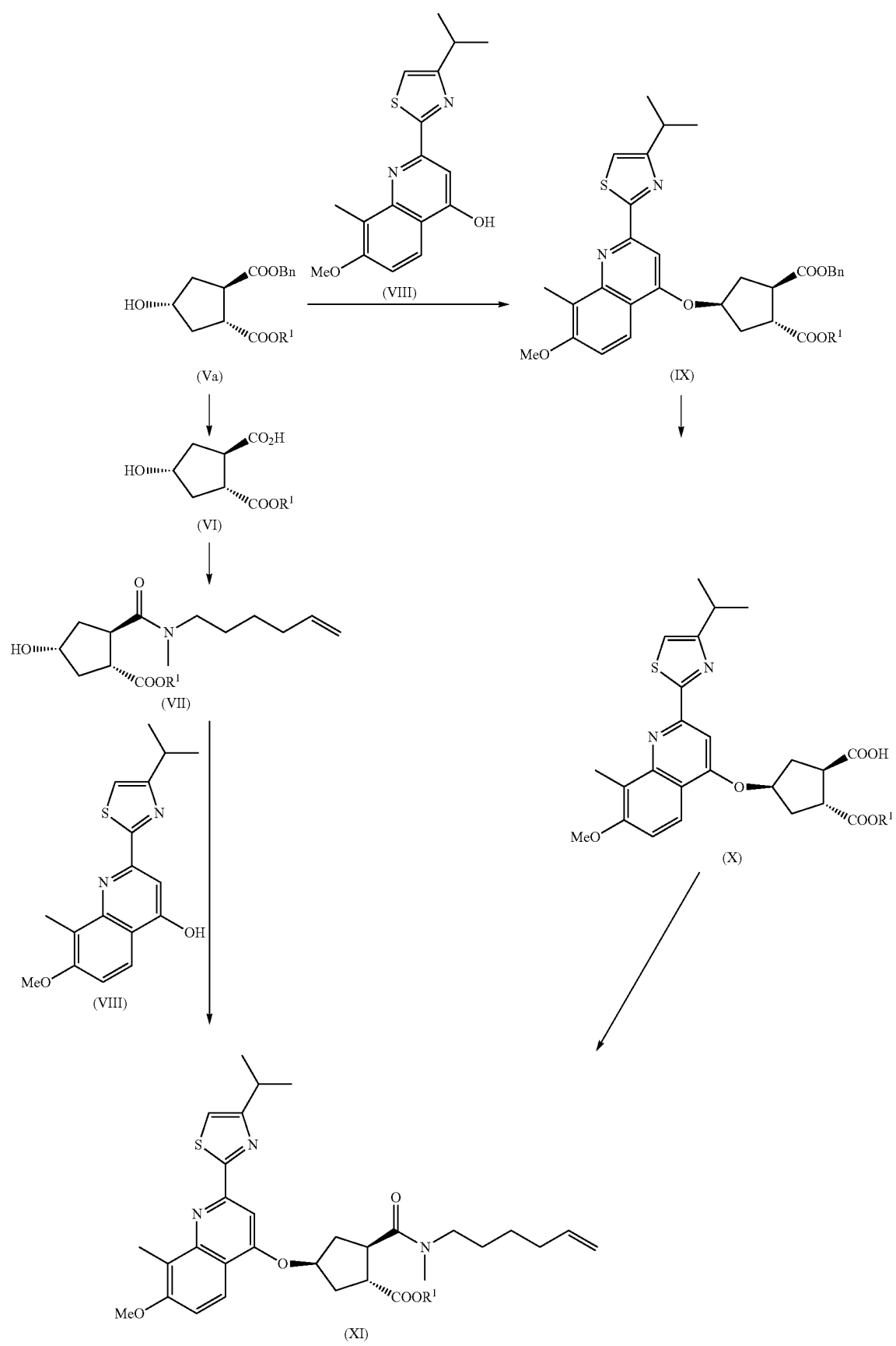

which intermediate (XI) is hydrolyzed to the acid (XII), which in turn is coupled with the cyclopropylamino acid ester (XIII) to obtain the desired end product (XIV), as outlined in the following reaction scheme:

function to an alcohol, thus obtaining 4-hydroxy-cyclopentyl-1,2-bis-carboxylic acid (II), which in turn is cyclized to the bicyclic lactone (III), wherein the carboxylic acid group in the bicyclic lactone (III) is esterified with benzyl alcohol thus

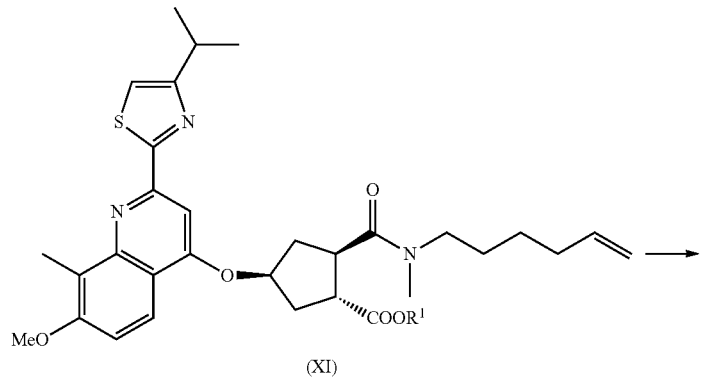

(XI)

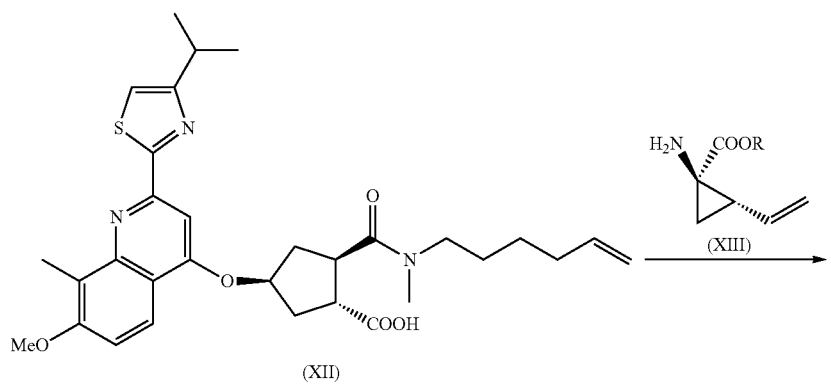

(XII)

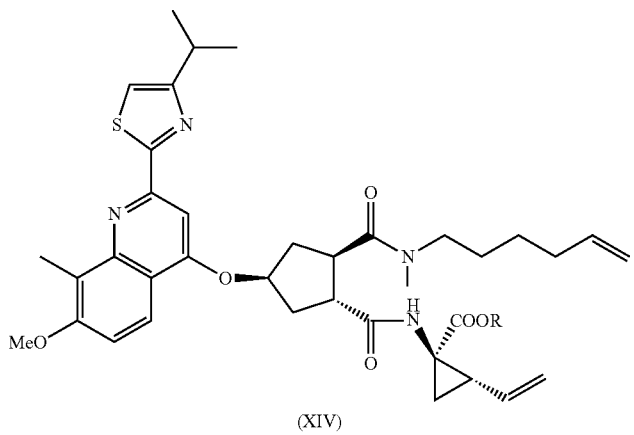

(XIV)

wherein R is $C_{1-4}$alkyl, and $R^1$, independently from R, is also $C_{1-4}$alkyl.

5. A process according to claim 1, wherein the compound of formula (XIV) is prepared by a process comprising a process for preparing intermediate (Va), starting from 4-oxo-cyclopentyl-1, 2-bis-carboxylic acid (I), by reducing the keto obtaining the lactone benzyl ester (IV), wherein the lactone is opened and the thus formed carboxylic acid group is esterified with a $C_{1-4}$alkanol thus yielding the hydroxycyclopentyl bis-ester of formula (V), which in turn is resolved in stereoisomers (Vb) and (Va); as outlined in the following reaction scheme, wherein $R^1$ represents $C_{1-4}$alkyl:

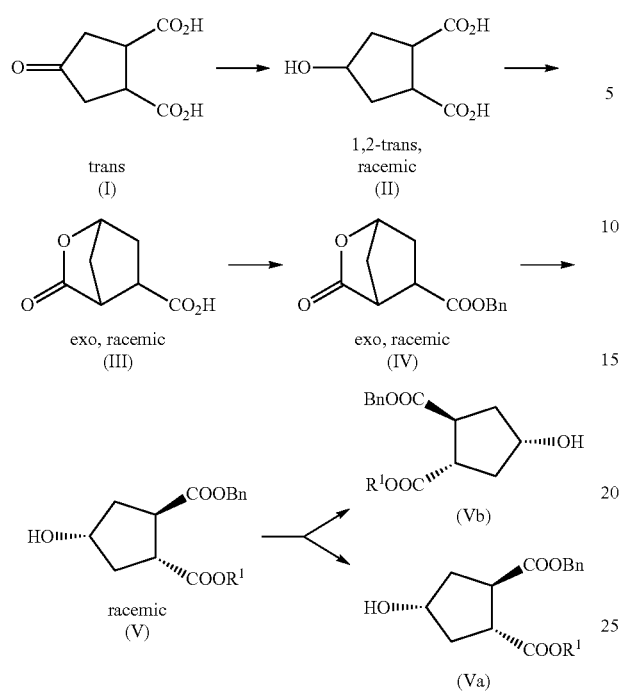

followed by either (a) reacting the hydroxycyclopentyl bis-ester of formula (Va) with a thiazolyl substituted quinolinol (VIII) in an ether forming reaction, thus obtaining a quinolinyloxy-cyclopentyl bis-ester of formula (IX), wherein the ester group that is in cis position vis-á-vis the ether group in the quinolinyloxy-cyclopentyl bis-ester of formula (IX) is selectively cleaved to a mono carboxylic acid (X), which in turn is coupled with an alkenylamine in an amide forming reaction, thus obtaining the desired product of formula (XI); or (b) selectively converting the hydroxycyclopentyl bis-ester of formula (Va) to the mono carboxylic acid (VI), which in turn is coupled with an alkenylamine in an amide forming reaction to obtain hydroxycyclopentylamide (VII), which in turn is reacted with a thiazolyl substituted quinolinol (VIII), thus obtaining the desired product of formula (XI); as outlined in the following reaction scheme, wherein $R^1$ represents $C_{1-4}$alkyl:

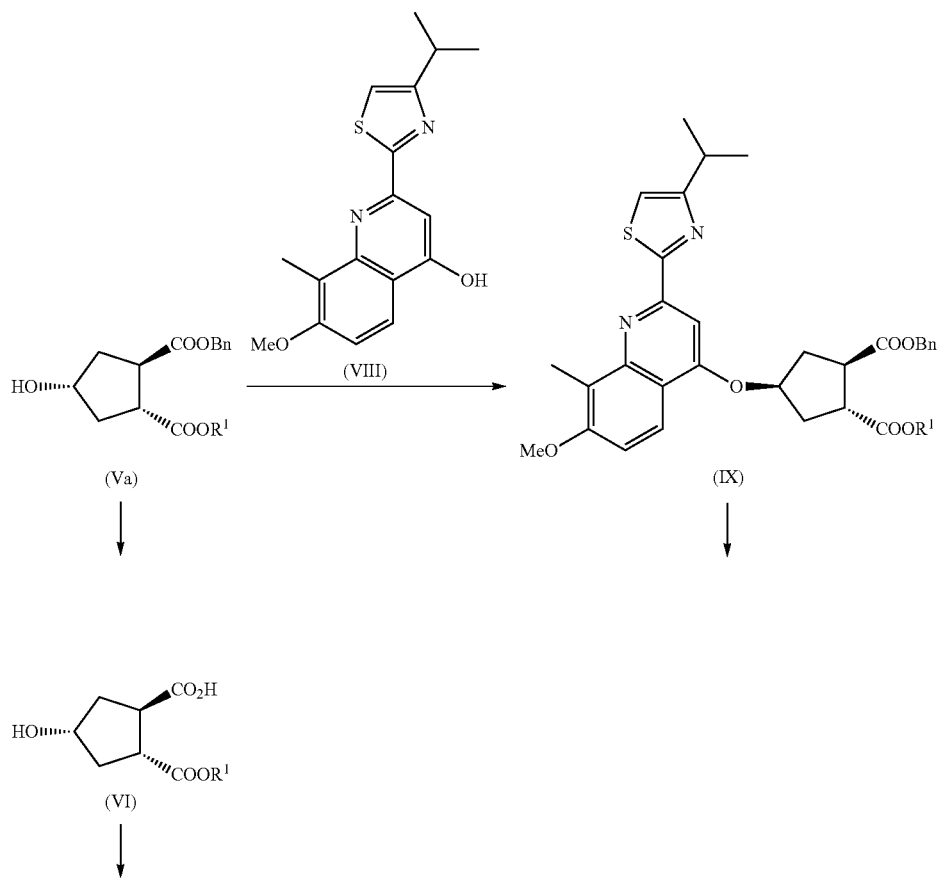

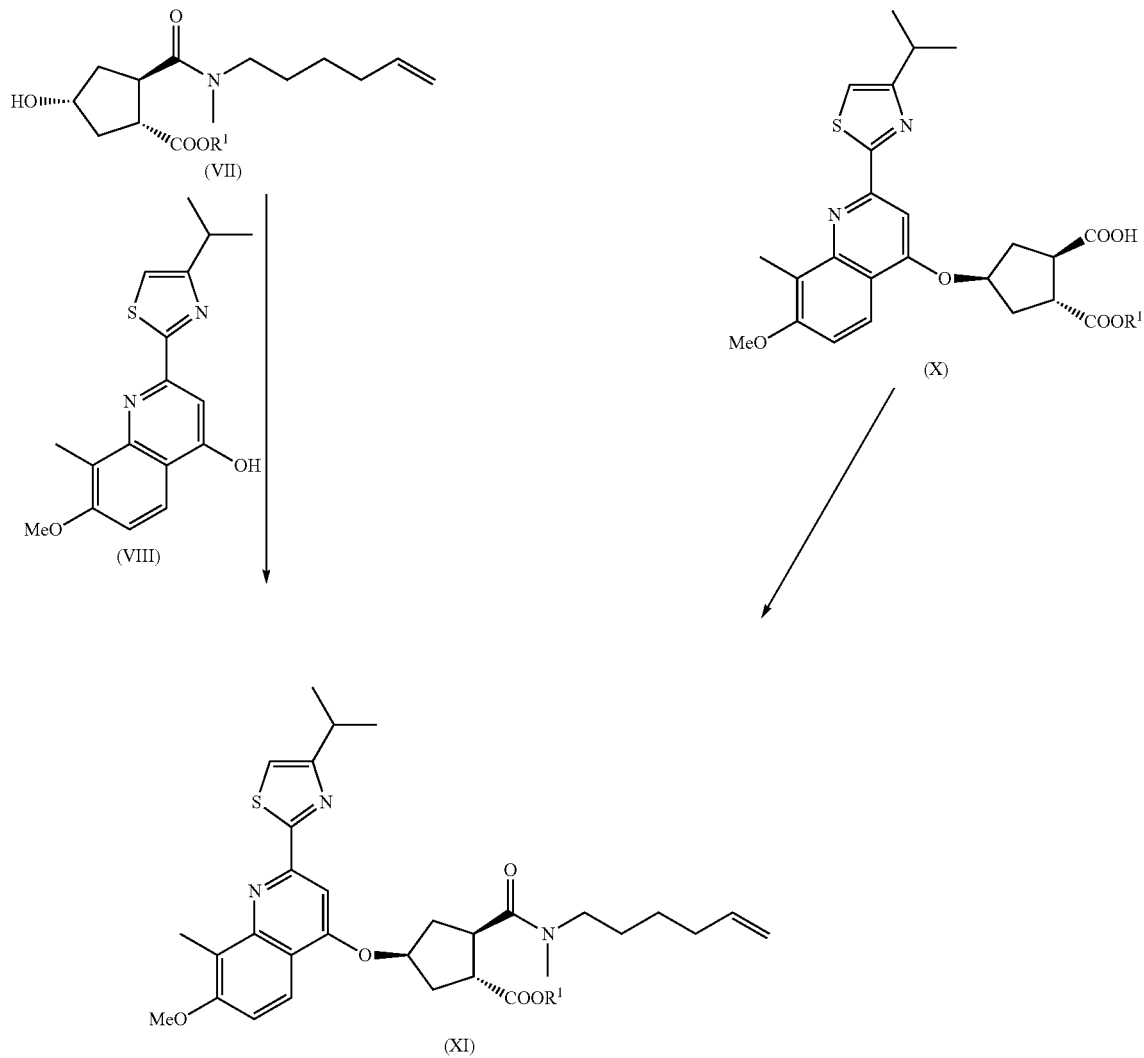
which intermediate (XI) is hydrolyzed to the acid (XII), which in turn is coupled with the cyclopropylamino acid ester (XIII) to obtain the desired end product (XIV), as outlined in the following reaction scheme:
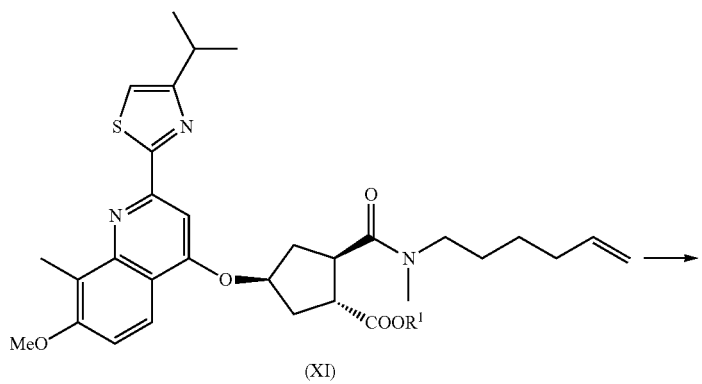

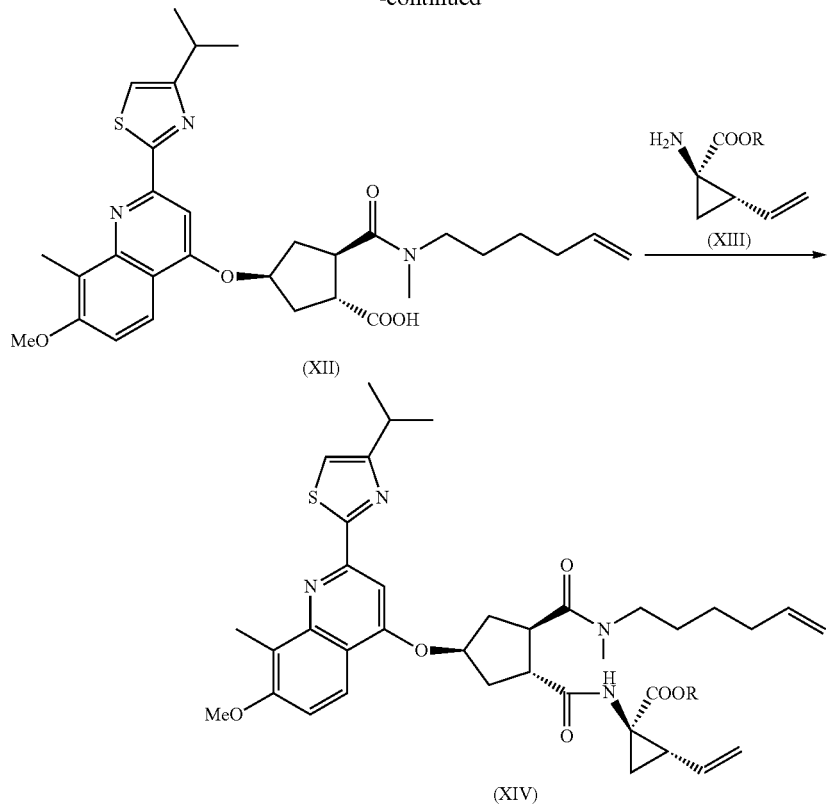

wherein R is C$_{1-4}$alkyl, and R$^1$, independently from R, is also C$_{1-4}$alkyl.

6. The process according to claim 4, wherein the compound of formula (IX) or of formula (XI) is obtained by reacting the compound of formula (Va), respectively of formula (VII), with the compound of formula (VIII), in the presence of an azodicarboxylate of formula R'OOC-N=N-COOR', a phosphine of formula R"$_3$P, and an organic solvent; wherein
R' represents ethyl or isopropyl or t-butyl;
R" represents, each independently, phenyl, 2-pyridyl, 3-pyridyl or 4-pyridyl.

7. The process according to claim 4, wherein the compound of formula (VII) or of formula (XI) is obtained by reacting compound of formula (VI), respectively compound of formula (X), with N-methylhex-5-enylamine (NMHA) and an amide-coupling agent in a reaction-inert solvent.

8. The process according to claim 7 wherein the amide-coupling agent is selected from EEDQ, IIDQ, EDCI, DCC, or 1,3-diisopropylcarbodiimide.

9. The process according to claim 4, wherein the compound of formula (VI) or the compound of formula (X) is obtained by reacting the compound of formula (Va), respectively compound (IX), with a reducing agent, in a reaction-inert solvent.

10. The process of claim 9, wherein the reducing agent is hydrogen in the presence of a metal catalyst, or wherein the reducing agent is formic acid or a salt thereof, a mixture of formic acid and a salt thereof, triethylsilane, t-butyldimethylsilane, phenylsilane, or poly(methylhydrosiloxane)optionally in the presence of a base.

11. The process according to claim 10, wherein the reducing agent is hydrogen in the presence of a metal catalyst.

12. The process according to claim 11, wherein the catalyst is selected from palladium on charcoal, palladium hydroxide on charcoal, palladium acetate, or palladium chloride.

13. The process according to claim 10, wherein the base is a triC$_{1-4}$alkylamine.

14. The process according to claim 9 wherein the organic solvent is selected from THF, MeTHF, acetic acid, toluene, or any mixture thereof.

15. The process according to claim 5, wherein the compound of formula (Va) is obtained by separating the mixture (V) by a chiral separation.

16. The process according to claim 15, wherein the chiral separation is by chiral column chromatography.

17. The process according to claim 5, wherein the compound of formula (V) is obtained by reacting compound of formula (IV) with C$_{1-4}$alkanol and an acid catalyst.

18. The process according to claim 5, wherein the compound of formula (IV) is obtained by reacting compound of formula (III) with benzyl alcohol; in the presence of a coupling agent; or in the presence of an C$_{1-4}$alkylchloroformate of the formula ClCOOR", wherein R" is C$_{1-4}$alkyl, such as methyl, ethyl, 1-propyl, 1-butyl, 2-butyl, and an organic base.

19. The process according to claim 18, wherein the coupling agent is selected from EDCI, DCC, and diisopropylcarbodiimide.

20. The process according to claim 5, wherein the compound of formula (III), or a salt thereof, is obtained by reacting compound of formula (II) or a salt thereof, with a C$_{1-4}$alkylchloroformate of the formula ClCOOR", wherein R" is as defined in claim 18; in the presence of an organic base.

21. The process according to claim 5, wherein the compound of formula (II) is obtained by reacting compound of formula (I) with hydrogen in the presence of a metal catalyst, optionally in the presence of a base.

22. The process according to claim 21, wherein the catalyst is selected from rhodium on charcoal, rhodium on alumina, platinum on charcoal, or platinum on alumina.

23. The process according to claim 20 wherein the base is selected from sodium hydroxide, alumina, and a triC$_{1-4}$alkylamine.

24. The process according to claim 1, wherein R$^1$ is methyl.

25. The process according to claim 1, wherein R is ethyl.

* * * * *